(12) United States Patent
King

US009358223B2

(10) Patent No.: US 9,358,223 B2
(45) Date of Patent: Jun. 7, 2016

(54) FORMULATION FOR PREVENTING OR REDUCING BLEEDING AT A SURGICAL SITE

(71) Applicant: WARSAW ORTHOPEDIC, INC., Warsaw, IN (US)

(72) Inventor: Vanja Margareta King, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/248,905

(22) Filed: Apr. 9, 2014

(65) Prior Publication Data

US 2014/0221447 A1 Aug. 7, 2014

Related U.S. Application Data

(62) Division of application No. 12/605,486, filed on Oct. 26, 2009, now abandoned.

(51) Int. Cl.
| | |
|---|---|
| *A61K 31/4168* | (2006.01) |
| *A61K 8/85* | (2006.01) |
| *A61K 9/70* | (2006.01) |
| *A61K 9/00* | (2006.01) |
| *A61K 9/16* | (2006.01) |
| *A61K 31/4164* | (2006.01) |
| *A61L 27/18* | (2006.01) |
| *A61L 27/34* | (2006.01) |
| *A61L 27/54* | (2006.01) |
| *A61L 31/06* | (2006.01) |
| *A61L 31/10* | (2006.01) |
| *A61L 31/16* | (2006.01) |
| *A61K 9/19* | (2006.01) |

(52) U.S. Cl.
CPC ........... *A61K 31/4168* (2013.01); *A61K 9/0019* (2013.01); *A61K 9/1641* (2013.01); *A61K 9/1647* (2013.01); *A61K 9/7007* (2013.01); *A61K 31/4164* (2013.01); *A61L 27/18* (2013.01); *A61L 27/34* (2013.01); *A61L 27/54* (2013.01); *A61L 31/06* (2013.01); *A61L 31/10* (2013.01); *A61L 31/16* (2013.01); *A61K 9/19* (2013.01); *A61L 2300/432* (2013.01); *A61L 2400/04* (2013.01)

(58) Field of Classification Search
CPC ......... A61L 27/18; A61L 27/34; A61L 31/06; A61L 31/10; A61L 2300/432; A61L 2400/04; A61L 27/54; A61L 31/16; A61K 31/4164; A61K 31/4168; A61K 9/0019; A61K 9/1641; A61K 9/1647; A61K 9/19; A61K 9/7007
See application file for complete search history.

(56) References Cited

U.S. PATENT DOCUMENTS

| | | | |
|---|---|---|---|
| 3,190,802 | A | 6/1965 | Zeile et al. |
| 3,020,660 | A | 8/1965 | Zeile et al. |
| 4,624,255 | A | 11/1986 | Schenck et al. |
| 4,765,974 | A | 8/1988 | Tokuda et al. |
| 4,863,457 | A | 9/1989 | Lee |
| 5,175,052 | A | 12/1992 | Tokuda et al. |
| 5,447,947 | A | 9/1995 | Campbell |
| 5,484,607 | A | 1/1996 | Horacek |
| 5,522,844 | A | 6/1996 | Johnson |
| 5,626,838 | A | 5/1997 | Cavanaugh, Jr. |
| 5,635,204 | A | 6/1997 | Gevirtz et al. |
| 5,759,583 | A | 6/1998 | Iwamoto et al. |
| 5,801,188 | A | 9/1998 | Hassenbusch, III et al. |
| 5,868,789 | A | 2/1999 | Huebner |
| 5,869,100 | A | 2/1999 | Horacek |
| 5,942,241 | A | 8/1999 | Chasin et al. |
| 5,942,503 | A | 8/1999 | Jung et al. |
| 5,942,530 | A | 8/1999 | Panetta et al. |
| 5,945,416 | A | 8/1999 | Shannon et al. |
| 5,980,927 | A | 11/1999 | Nelson et al. |
| 6,030,642 | A | 2/2000 | Horacek |
| 6,069,129 | A | 5/2000 | Sandberg et al. |
| 6,147,102 | A | 11/2000 | Borgman |
| 6,179,862 | B1 | 1/2001 | Sawhney |
| 6,248,345 | B1 | 6/2001 | Goldenheim et al. |
| 6,287,588 | B1 | 9/2001 | Shih et al. |
| 6,326,020 | B1 | 12/2001 | Kohane et al. |
| 6,331,311 | B1 | 12/2001 | Brodbeck et al. |
| 6,417,184 | B1 | 7/2002 | Ockert |
| 6,428,804 | B1 | 8/2002 | Suzuki et al. |

(Continued)

FOREIGN PATENT DOCUMENTS

| | | |
|---|---|---|
| WO | 03005961 A2 | 1/2003 |
| WO | 2006011915 A1 | 2/2006 |
| WO | 2006022611 A2 | 3/2006 |
| WO | 2006101540 A1 | 9/2006 |
| WO | WO 2008014066 A1 * | 1/2008 |
| WO | 2008079868 A1 | 7/2008 |
| WO | 2009100441 A2 | 8/2009 |
| WO | WO 2009129437 A2 * | 10/2009 |

OTHER PUBLICATIONS

Atrigel, Drug Delivery Platform, QLT USA, Inc., Revised Jul. 2006, 2 pages.
U.S. Appl. No. 12/056,511, filed Mar. 27, 2008.
U.S. Appl. No. 61/046,269, filed Apr. 18, 2008.

*Primary Examiner* — Abigail Fisher
(74) *Attorney, Agent, or Firm* — Sorell Lenna & Schmidt LLP

(57) ABSTRACT

An implantable drug depot useful for preventing, reducing or treating bleeding at a surgical site beneath the skin in a patient is provided. The implantable drug depot comprises a therapeutically effective amount of clonidine or a pharmaceutically acceptable salt thereof, and at least one biodegradable polymer. The drug depot is capable of releasing clonidine or a pharmaceutically acceptable salt thereof over a period of at least three days.

19 Claims, 13 Drawing Sheets

(56) References Cited

U.S. PATENT DOCUMENTS

| | | |
|---|---|---|
| 6,461,631 B1 | 10/2002 | Dunn et al. |
| 6,524,607 B1 | 2/2003 | Goldenheim et al. |
| 6,534,048 B1 | 3/2003 | Borgman |
| 6,534,081 B2 | 3/2003 | Goldenheim et al. |
| 6,589,549 B2 | 7/2003 | Shih et al. |
| 6,630,155 B1 | 10/2003 | Chandrashekar et al. |
| 6,632,457 B1 | 10/2003 | Sawhney |
| 6,756,058 B2 | 6/2004 | Brubaker et al. |
| 6,773,714 B2 | 8/2004 | Dunn et al. |
| 6,921,541 B2 | 7/2005 | Chasin et al. |
| 6,974,462 B2 | 12/2005 | Sater |
| 6,992,110 B2 | 1/2006 | Kranzler et al. |
| 7,144,412 B2 | 12/2006 | Wolf et al. |
| 7,166,570 B2 | 1/2007 | Hunter et al. |
| 7,220,281 B2 | 5/2007 | Lambrecht et al. |
| 7,229,441 B2 | 6/2007 | Trieu et al. |
| 7,235,043 B2 | 6/2007 | Gellman et al. |
| 7,287,983 B2 | 10/2007 | Ilan |
| 7,318,840 B2 | 1/2008 | McKay |
| 7,329,259 B2 | 2/2008 | Cragg |
| 7,345,065 B2 | 3/2008 | Gil et al. |
| 7,361,168 B2 | 4/2008 | Makower et al. |
| 7,367,978 B2 | 5/2008 | Drewry et al. |
| 7,507,398 B2 | 3/2009 | Rabinowitz et al. |
| 7,524,812 B2 | 4/2009 | Ellis et al. |
| 8,722,079 B2 * | 5/2014 | King .................... 424/426 |
| 8,946,277 B2 * | 2/2015 | Zanella et al. ............ 514/401 |
| 2002/0009454 A1 | 1/2002 | Boone et al. |
| 2002/0058656 A1 | 5/2002 | Ockert |
| 2002/0090398 A1 | 7/2002 | Dunn et al. |
| 2002/0094998 A1 | 7/2002 | Burke et al. |
| 2003/0022926 A1 | 1/2003 | Lavand'Homme |
| 2003/0087962 A1 * | 5/2003 | Demopulos et al. ......... 514/649 |
| 2003/0185873 A1 | 10/2003 | Chasin et al. |
| 2003/0204191 A1 | 10/2003 | Sater et al. |
| 2003/0224033 A1 | 12/2003 | Li et al. |
| 2004/0028726 A1 | 2/2004 | Fischer et al. |
| 2004/0072799 A1 | 4/2004 | Li et al. |
| 2004/0082540 A1 | 4/2004 | Hermida Ochoa |
| 2004/0101582 A1 | 5/2004 | Wolicki |
| 2004/0109893 A1 | 6/2004 | Chen et al. |
| 2004/0208917 A1 | 10/2004 | Fischer et al. |
| 2004/0214793 A1 | 10/2004 | Hermida Ochoa |
| 2004/0265364 A1 | 12/2004 | Ozturk et al. |
| 2005/0058696 A1 | 3/2005 | Donello et al. |
| 2005/0059744 A1 | 3/2005 | Donello et al. |
| 2005/0095277 A1 | 5/2005 | Ozturk et al. |
| 2005/0142163 A1 | 6/2005 | Hunter et al. |
| 2005/0175709 A1 | 8/2005 | Baty et al. |
| 2005/0186261 A1 | 8/2005 | Avelar et al. |
| 2005/0197293 A1 | 9/2005 | Mellis et al. |
| 2006/0074422 A1 | 4/2006 | Story et al. |
| 2006/0106361 A1 | 5/2006 | Muni et al. |
| 2006/0148903 A1 | 7/2006 | Burch et al. |
| 2006/0183786 A1 | 8/2006 | Wang |
| 2006/0189944 A1 | 8/2006 | Campbell et al. |
| 2006/0228391 A1 | 10/2006 | Seyedin et al. |
| 2007/0156180 A1 | 7/2007 | Jaax et al. |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2007/0248639 A1 | 10/2007 | Demopulos et al. |
| 2007/0253994 A1 | 11/2007 | Hildebrand |
| 2008/0091207 A1 | 4/2008 | Truckai et al. |
| 2008/0152709 A1 | 6/2008 | Bortz |
| 2008/0171075 A1 | 7/2008 | Ozturk et al. |
| 2009/0263451 A1 * | 10/2009 | King ................... 424/423 |
| 2009/0264489 A1 * | 10/2009 | Hildebrand et al. ......... 514/401 |
| 2010/0239632 A1 * | 9/2010 | Walsh .............. A61K 9/0024 424/423 |
| 2012/0029042 A1 * | 2/2012 | King ................... 514/401 |

* cited by examiner

FORMULATION FOR PREVENTING OR REDUCING BLEEDING AT A SURGICAL SITE

The present application is a divisional application of U.S. patent application Ser. No. 12/605,486, filed Oct. 26, 2009. The entire disclosure of which is herein incorporated by reference into the present disclosure.

BACKGROUND

Surgery has always been a vital part of modern medicine to treat certain conditions that other interventional means cannot. However, surgical procedures are not without significant complications including bleeding at the surgical site following the procedure. For example, bleeding commonly occurs following a Whipple procedure which is a major surgery that involves the removal of the head of the pancreas to treat pancreatic cancer, in addition, bleeding is a common complication following oral surgery and thyroid surgery. Bleeding can occur following most surgeries resulting in further complications. To prevent the build-up of blood at surgical sites following surgery, drains or small tubes are typically placed at a surgical site prior to closing the surgical site to allow for the discharge of blood from bleeding following a surgical procedure. However, the use of a drain can be uncomfortable for the patient and the discharge of blood can be unpleasant as well. As such, there is a need to develop an effective treatment to prevent bleeding at a surgical site following a surgical procedure.

One pharmaceutical that is known to the medical profession is clonidine, which is widely recognized as an antihypertensive agent that acts as an agonist on the alpha-2-adrenergic receptor and as a neural receptor agonist. In general, clonidine also referred to as 2,6-dichloro-N-2-imidazolidinyldenebenzenamine ($C_9H_9Cl_2N_3$) may be represented by the following chemical structure:

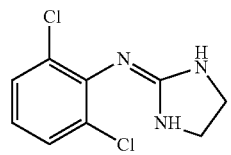 [SMILES: Clc1cccc(Cl)c1N=C1NCCN1]

Clonidine has been shown to effectively regulate blood pressure in the perioperative period in patients undergoing rhytidectomy. Beninger et al., "Clonidine in the Management of Blood Pressure During Rhytidectomy," *Asethet. Surgical Journal*, 18(2): 89-94. However, to date, sustain release clonidine depot formulations have not been developed to prevent, reduce and/or treat bleeding following a surgical procedure.

SUMMARY

Novel compositions and methods are provided for effectively preventing, reducing and/or treating bleeding at a surgical site during and after surgery. The treatment may last for extended periods of time and bleeding may be prevented or reduced for extended periods of time.

In one exemplary embodiment, an implantable drug depot useful for preventing, reducing or treating bleeding at a surgical site beneath the skin in a patient is provided. The implantable drug depot comprises a therapeutically effective amount of clonidine or pharmaceutically acceptable salt thereof, and at least one biodegradable polymer. The drug depot is implantable locally at the surgical site to reduce, prevent or treat bleeding. The drug depot is capable of releasing clonidine or pharmaceutically acceptable salt thereof over a period of at least three days. The polymer comprises one or more of poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone or a combination thereof. In various embodiments, the drug depot releases (i) a bolus dose of the clonidine or pharmaceutically acceptable salt thereof at the surgical site over a first period of up to 48 hours and (ii) an effective amount of the clonidine or pharmaceutically acceptable salt thereof over a subsequent period of at least 3 days.

In another exemplary embodiment, an implantable drug depot useful for reducing, preventing or treating bleeding at a surgical site beneath the skin in a patient is provided wherein the implantable drug depot comprises a therapeutically effective amount of clonidine or pharmaceutically acceptable salt thereof and a polymer, the drug depot is implantable locally at the surgical site to reduce, prevent or treat bleeding, and the depot is capable of releasing (i) about 5% to about 45% of the clonidine relative to the total amount of the clonidine loaded in the drug depot over a first period of up to 48 hours and (ii) about 55% to about 99% of the clonidine relative to the total amount of the clonidine loaded in the drug depot over a subsequent period of at least 3 days.

In still yet another exemplary embodiment, a method of preventing or treating bleeding at a surgical site in a patient is provided. The method comprises administering one or more biodegradable drug depots comprising a therapeutically effective amount of clonidine or pharmaceutically acceptable salt thereof locally to a surgical site to prevent or treat bleeding at the surgical site, wherein the drug depot releases an effective amount of the clonidine over a period of at least 3 days. In various embodiments, the one or more biodegradable drug depots release (i) a bolus dose of the clonidine or pharmaceutically acceptable salt thereof at the surgical site over a first period of up to 48 hours and (ii) an effective amount of the clonidine or pharmaceutically acceptable salt thereof over a subsequent period of at least 3 days.

Clonidine in the various embodiments may be in the form of a salt. One example of a salt is a hydrochloric salt. In various embodiments, clonidine may be in the form of a base. Further, clonidine or a pharmaceutically acceptable salt thereof may be encapsulated in a plurality of depots comprising microparticles, microspheres, microcapsules, and/or microfibers which could be suspended in a gel. The drug depot may be a ribbon, pellet, film or strip. The drug depot can also be a gel formulation. The drug depot may be disposed on or within a medical device and in various embodiments, the drug depot may be a coating disposed on a medical device.

The polymer in various embodiments may comprise about 60% to about 90% of the total wt. % of the drug depot. In some embodiments, the polymer may comprise about 70% to about 90% of the total wt. % of the drug depot. The polymer is capable of degrading or degrades in 30 days or less after the drug depot is implanted at the site. In various embodiments, the polymer may comprise poly(lactic-co-glycolic acid) and the poly(lactic-co-glycolic acid) comprises a mixture of polyglycolide and polylactide. The mixture comprises more polylactide than polyglycolide.

The polymer in various embodiments may comprise one or more of poly(lactide-co-glycolide), polylactide, polyglycolide, D-lactide, D,L-lactide, L-lactide, D,L-lactide-co-ε-caprolactone, D,L-lactide-co-glycolide-co-ε-caprolactone or a combination thereof.

The drug depot in various embodiments is capable of preventing, reducing or treating bleeding at a surgical site within 6 hours, 5 hours, 4 hours, 3 hours, 2 hours, 1 hour, 30 minutes or 15 minutes after implantation.

The drug depot in various embodiments is capable of releasing between 0.05 microgram (ug) and 3 milligram (mg) per day of clonidine or pharmaceutically acceptable salt thereof to prevent, reduce or treat bleeding at a surgical site in a patient. The drug depot is capable of releasing between 0.05 microgram (ug) and 3 milligram (mg) per day of clonidine or pharmaceutically acceptable salt thereof for at least 1 day, at least 3 days, at least 3 to 7 days, at least 3 to 10 days and at least 3 to 30 days.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
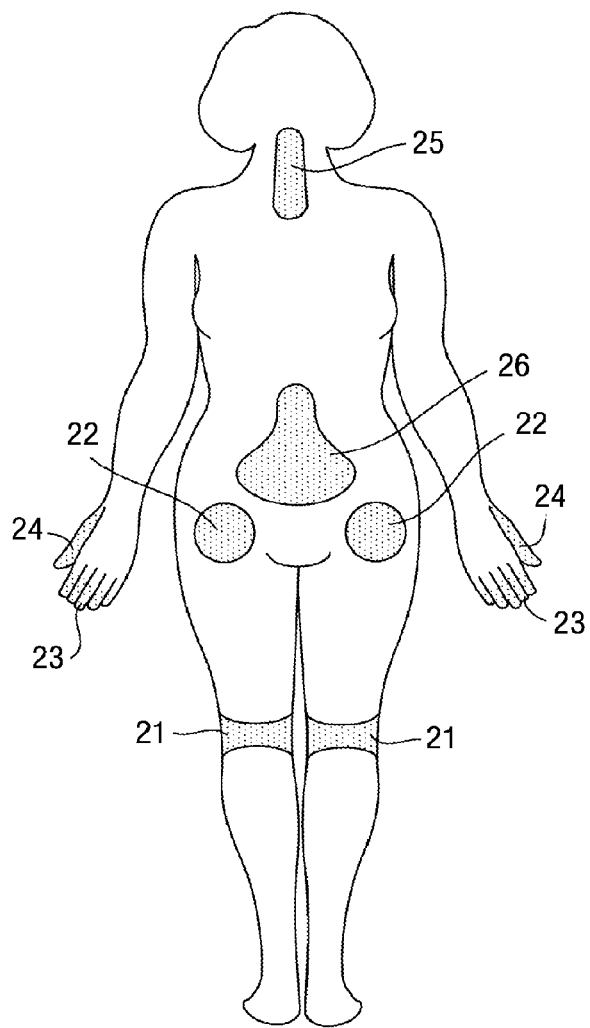
FIG. 1 illustrates a number of common locations within a patient that may be sites at which surgery may occur and locations at which a drug depot or the medical device containing clonidine can locally be administered thereto to prevent, reduce and/or treat bleeding.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

DEFINITIONS

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

A "drug depot" is the composition in which the biologically active agent is administered to the surgical site. Thus, a drug depot may comprise a physical structure to facilitate implantation and retention in a desired site. The drug depot may also comprise the biologically active agent or drug itself. The term "drug" as used herein is generally meant to refer to any substance that alters the physiology of a patient. The term "drug" may be used interchangeably herein with the terms "biologically active agent," "therapeutic agent," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.01 cm to about 10 cm from the administration site and comprises clonidine.

A "depot" includes but is not limited to capsules, microspheres, microparticles, microcapsules, microfibers, particles, nanospheres, nanoparticles, coating, matrices, wafers, pills, pellets, emulsions, a pump, liposomes, micelles, gels, fibers, ribbons, strips, sheets or other pharmaceutical delivery compositions or a combination thereof.

A "therapeutically effective amount" or "effective amount" is such that when administered, the drug results in alteration of the biological activity, such as, for example, inhibition or reduction of bleeding at a surgical site during or after surgery, etc. The dosage administered to a patient can be single or multiple doses depending upon a variety of factors, including the drug's administered pharmacokinetic properties, the route of administration, patient conditions and characteristics (sex, age, body weight, health, size, etc.), concurrent treatments, frequency of treatment and the effect desired. In some embodiments, the formulation is designed for immediate release. In other embodiments, the formulation is designed for sustained release. In other embodiments, the formulation comprises one or more immediate release surfaces and one or more sustained release surfaces.

The term "biodegradable" includes that all or parts of the drug depot will degrade over time by the action of enzymes, by hydrolytic action and/or by other similar mechanisms in the human body. In various embodiments, "biodegradable" includes that the depot (e.g., strip, film, fiber, microparticle, microsphere, etc.) can break down or degrade within the body to non-toxic components after or while a therapeutic agent has been or is being released. By "bioerodible," it is meant that the depot will erode or degrade over time due, at least in part, to contact with substances found in the surrounding tissue, fluids or by cellular action. By "bioabsorbable," it is meant that the depot will be broken down and absorbed within the human body, for example, by a cell or tissue. "Biocompatible" means that the depot will not cause substantial tissue irritation or necrosis at the target tissue site.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s). As persons of ordinary skill are aware, sustained release formulations may, by way of example, be created as films, slabs, sheets, pellets, microparticles, microspheres, microcapsules, spheroids, shaped derivatives or paste. The formulations may be in a form that is suitable for suspension in isotonic saline, physiological buffer or other solution acceptable for injection into a patient. Further, the formulations may be used in conjunction with any implantable, insertable or injectable system that a person of ordinary skill would appreciate as useful in connection with embodiments herein including but not limited to parenteral formulations, microspheres, microcapsules, gels, pastes, implantable rods, pellets, plates, filters, matrices, ribbons, strips, or fibers, etc.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Immediate release refers to the release of drug within a short time period following administration, e.g., generally within a few minutes to about 1 hour.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

The phrase "release rate profile" refers to the percentage of active ingredient that is released over fixed units of time, e.g., mcg/hr, mcg/day, mg/hr, mg/day, 10% per day for ten days, etc. As persons of ordinary skill know, a release rate profile may be but need not be linear. By way of a non-limiting example, the drug depot may be a strip or film that releases clonidine over a period of time.

The term "alpha adrenergic agonist" as used herein refers to any compound that binds to and/or activates and/or agonizes at least one or more alpha-adrenergic receptor or its subtypes to any degree and/or stabilizes at least one or more alpha-adrenergic receptor or its subtypes in an active or inactive conformation. Thus, by the term alpha-adrenergic receptor agonist, it is meant to include partial agonists, inverse agonists, as well as complete agonists of one or more alpha-adrenergic receptors or its subtypes.

Treating or treatment of a condition refers to executing a protocol, which may include administering one or more drugs to a patient (human, normal or otherwise, or other mammal), in an effort to alleviate signs or symptoms of the condition (e.g., bleeding at the surgical site). Alleviation can occur prior to signs or symptoms of the condition appearing as well as after its appearance. Thus, "treating" or "treatment" includes "preventing" or "prevention" of disease or undesirable condition. In addition, "treating" or "treatment" does not require complete alleviation of signs or symptoms and specifically includes protocols that have only a marginal effect on the patient. "Reducing bleeding" includes a decrease in the bleeding during or following surgery at the surgical site and does not require complete alleviation of bleeding. In various embodiments, reducing bleeding includes even a marginal decrease in the amount of the bleeding at the surgical site. By way of example, the administration of an effective dosage of clonidine may be used to prevent, treat or reduce the amount of bleeding at the surgical site following surgery.

"Localized" delivery includes delivery where one or more drugs or devices are deposited at a surgical site, for example, within a tissue, a nerve root of the nervous system or a region of the brain, or in close proximity (within about 5 cm, or within about 1 cm, or within 0.1 cm for example) thereto. A "targeted delivery system" provides delivery of one or more drug depots, gels or a depot dispersed in the gel having a quantity of therapeutic agent that can be deposited at or near a surgical site as needed to reduce, prevent or treat bleeding at the surgical site.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "G" refers to polyglycolide.

The abbreviation "PEG" refers to poly(ethylene glycol).

The abbreviation "PLGA" refers to poly(lactide-co-glycolide) also known as poly(lactic-co-glycolic acid), which are used interchangeably.

The abbreviation "PLA" refers to polylactide.

The abbreviation "POE" refers to poly(orthoester).

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

Clonidine

The methods and compositions of the present application utilize clonidine which is an alpha adrenergic agonist. In general, the chemical name of clonidine is 2,6-dichloro-N-2-imidazolidinyldenebenzenamine ($C_9H_9Cl_2N_3$). Clonidine has a molecular weight of 230.09 and exhibits the following general structure:

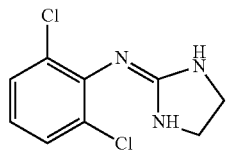 [SMILES: Clc1cccc(Cl)c1N=C1NCCN1]

Unless otherwise specified or apparent from context, where this specification and the set of claims that follows refer to clonidine, it is understood that the inventors are also referring to pharmaceutically acceptable salts. One well-known commercially available salt for clonidine is its hydrochloride salt. Some other examples of potentially pharmaceutically acceptable salts include those salt=forming acids and bases that do not substantially increase the toxicity of a compound, such as, salts of alkali metals such as magnesium, potassium and ammonium, salts of mineral acids such as hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, and the like.

Further, when referring to clonidine, the active ingredient may not only be in the salt form, but also in the base form (e.g., free base). In various embodiments, if it is in the base form, it may be combined with polymers under conditions in which there is not severe polymer degradation, as may be seen upon heat or solvent processing that may occur with PLGA or PLA. By way of a non-limiting example, when formulating clonidine with poly(orthoesters), it may be desirable to use the clonidine base formulation. By contrast, when formulating clonidine with PLGA, it may be desirable to use the HCl salt form. In various embodiments, clonidine may be in the form of a combination of a salt and a base. Clonidine or a pharmaceutically acceptable salt thereof is available from various pharmaceutical manufacturers.

In various embodiments, the therapeutically effective amount of clonidine comprises from about 0.1 ug/day to 100 mg/day. In some embodiments, the therapeutically effective amount of clonidine comprises from about 30 ug to 1 mg of clonidine per day. In some embodiments, the therapeutically effective amount of clonidine comprises from about 30 ug to 2.4 mg of clonidine per day. In some embodiments, the therapeutically effective amount of clonidine comprises from about 0.1 mg to 0.3 mg of clonidine per day. In some embodiments, the therapeutically effective amount of clonidine or dosage comprises 0.0005 ug, 0.001 ug, 0.0025 ug, 0.005 ug, 0.1 ug, 0.2 ug, 0.3 ug, 0.4 ug, 0.5 ug, 0.6 ug, 0.7 ug, 0.8 ug, 0.9 ug, 1 ug, 10 ug, 20 ug, 30 ug, 40 ug, 50 ug, 60 ug, 70 ug, 80 ug, 90 ug, 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 30 mg, 35 mg, or 40 mg (and all ranges and subranges therebetween) of clonidine per day. In one embodiment, the dosage to a human is between 0.1 mg and 0.3 mg of clonidine per day.

In some embodiments, local administration of the drug depot at or near the target tissue (surgical) site allows for a lower dose of clonidine to be used than if administered orally, intravenously or intramuscularly. For example, local administration of the drug depot can be accomplished with daily doses that are 20%, 15%, 10%, 5%, 1%, 0.5%, 0.1%, 0.01% of an oral, intravenous or intramuscular dose. In turn, systemic side effects, such as for example, liver transaminase elevations, hepatitis, liver failure, myopathy, constipation, etc., may be minimized or eliminated.

Therapeutic Agents

In addition to clonidine, the drug depot may comprise one or more additional therapeutic agents. Examples of therapeutic agents include those that are direct-acting and local-acting modulators of pro-inflammatory cytokines such as TNF-α and IL-1 including, but not limited to, soluble tumor necrosis factor α receptors, any pegylated soluble tumor necrosis factor α receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1→3-β-D-glucans, Lenercept, PEG-sTNFRII Fc Mutein, D2E7, Afelimomab, and combinations thereof. In other embodiments, a therapeutic agent includes metalloprotease inhibitors, glutamate antagonists, glial cell-derived neurotropic factors (GDNF), B2 receptor antagonists, Substance P receptor (NK1) antagonists such as capsaicin and civamide, downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines, TNF binding protein, onercept (r-hTBP-1), recombinant adeno-associated viral (rAAV) vectors encoding inhibitors, enhancers, potentiators, or neutralizers, antibodies, including but not limited to naturally occurring or synthetic, double-chain, single-chain, or fragments thereof. For example, suitable therapeutic agents include molecules that are based on single chain antibodies called Nanobodies™ (Ablynx, Ghent Belgium), which are defined as the smallest functional fragment of a naturally occurring, single-domain antibody. Alternatively, therapeutic agents include, agents that effect kinases and/or inhibit cell signaling mitogen-activated protein kinases (MAPK), p38 MAPK, Src or protein tyrosine kinase (PTK). Therapeutic agents include, kinase inhibitors such as, for example, Gleevec, Herceptin, Iressa, imatinib (STI571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor. RWJ67657 (J&J), UO126, Gd, SCIO-469 (Scios), RO3201195 (Roche), Semipimod (Cytokine Pharma-Sciences), or derivatives thereof.

Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin 11, which upregulates TNF-α), interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as glucocorticoids; antioxidants, such as dithiocarbamate, and other compounds, such as, for example, sulfasalazine.

Specific examples of therapeutic agents suitable for use include, but are not limited to, an anti-inflammatory agent, analgesic agent, or osteoinductive growth factor or a combination thereof. Anti-inflammatory agents include, but are not limited to, salicylates, diflunisal, sulfasalazine, indomethacin, ibuprofen, naproxen, tolmetin, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as statins and steroids. Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisol, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof. Exemplary statins include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171, the entire disclosures of which are herein incorporated by reference), fluvastatin, lovastatin, rosuvastatin and fluindostatin (Sandoz XU-62-320), dalvastain (EP Appln. Pubin. No. 738510 A2, the entire disclosure is herein incorporated by reference), eptastatin, pitavastatin, or pharmaceutically acceptable salts thereof or a combination thereof. In various embodiments, where a statin is included in a depot, the statin may comprise mixtures of (+)R and (−)-S enantiomers of the statin. In various embodiments, the statin may comprise a 1:1 racemic mixture of the statin.

Suitable anabolic growth or anti-catabolic growth factors include, but are not limited to, a bone morphogenetic protein, a growth differentiation factor, a LIM mineralization protein, CDMP or progenitor cells or a combination thereof.

Analgesic agents may also be included in the depot: Suitable analgesic agents include, but are not limited to, acetaminophen, bupivacaine, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Suitable analgesics also include agents with analgesic properties, such as for example, amitriptyline, carbamazepine, gabapentin, pregabalin or a combination thereof.

The depot may contain a muscle relaxant. Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium or combinations thereof.

Drug Depot

In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. In various embodiments, the drug depot may not be biodegradable or comprise material that is not biodegradable. Non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly-ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers or combinations thereof.

In various embodiments, the depot may comprise at least one analgesic agent and a biodegradable biopolymer that may provide immediate release or sustained release of the at least one analgesic agent and/or at least one anti-inflammatory agent. Examples of suitable sustained release biopolymers include but are not limited to poly(alpha-hydroxy acids), poly(lactide-co-glycolide) (PLGA or PLG), polylactide (PLA), polyglycolide (PG), polyethylene glycol (PEG) conjugates of poly(alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407. PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations.

In some embodiments, these biopolymers may also be coated on the drug depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot. In some embodiments, the range of the coating on the drug depot ranges from about 5 microns to about 250 microns or 5 microns to about 200 microns to delay release from the drug depot.

Where different combinations of polymers are used (bi, tri (e.g., PLGA-PEO-PLGA) or terpolymers), they may be used in different molar ratios, 1:1, 2:1, 3:1, 4:1, 5:1, 6:1, 7:1, 8:1, 9:1, or 10:1.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

The drug depot may comprise non-resorbable polymers as well. These non-resorbable polymers can include, but are not limited to, delrin, polyurethane, copolymers of silicone and polyurethane, polyolefins (such as polyisobutylene and polyisoprene), acrylamides (such as polyacrylic acid and poly (acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. In some embodiments, the drug depot may comprise PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of drug depots may need to be removed.

The drug depot may be the medical device itself or be part of the medical device and thereby coated on the medical device. Examples of the medical device, include, but are not limited to, a prosthetic device for hard tissue such as an artificial hip joint, an artificial elbow joint, an artificial knee joint, an artificial shoulder joint, an artificial dental root, an artificial corpus vertebrae, a bone prosthetic member, a device which facilitates tissue regeneration, a sponge or a sponge containing a ceramic component, a cage, a stent, an artificial valve, a metal plate, a filter, etc. Regardless of the design of the medical device, the drug depot containing clonidine can be coated on all surfaces of the medical device or on a portion of the medical device so as to adequately supply in the desired amount clonidine to the desired target surgical site. In some embodiments, the entire inner and outer surfaces of the medical device may be coated with clonidine in therapeutic dosage amounts. In some embodiments, the coatings may be on the outer surface, the ends, or one end of the medical device. The coating could be a few microns up to a few millimeters thick. If used to deliver a systemically relevant level, it could also be expected to treat bleeding at distant sites. The coating may be applied to the implant via a conventional coating process such as impregnating coating, spray coating and dip coating.

In various embodiments, the depot can be designed to cause an initial burst dose of therapeutic agent within the first 30 minutes, hour, 2 hours, 5 hours, 10 hours, 24 hours, 2 days, 3 days, 4 days, or 5 days after implantation. "Initial burst" or "burst effect" or "bolus dose" refer to the release of therapeutic agent from the depot during the first 30 minutes, hour, 2 hours, 5 hours, 10 hours, 24 hours, 2 days, 3 days, 4 days, or 5 days after the depot comes in contact with an aqueous fluid (e.g., synovial fluid, cerebral spinal fluid, etc.). This burst effect is particularly beneficial for preventing, reducing and/or treating bleeding at a surgical site. The "burst effect" is believed to be due to the increased release of therapeutic agent from the depot. In alternative embodiments, the depot (e.g., gel, pellet, wafer, etc.) is designed to avoid this initial burst effect if bleeding is anticipated at a significant time following surgery. In other alternative embodiments, the depot is designed to have an immediate release which is a bolus dose within the first hour after implantation.

In various embodiments, the release of clonidine and any additional therapeutic agents may be for at least one, at least two, at least three, at least four, at least five, at least six, at least seven, at least eight, at least nine, at least ten, at least eleven, at least twelve, at least thirteen, at least fourteen or at least fifteen days or longer.

In one embodiment, clonidine is administered in an amount of about 0.0001 mg/kg/day to about 40 mg/kg/day for reducing, preventing and/or treating bleeding at a surgical site. In another embodiment, clonidine is administered in an amount of about 0.001 mg/kg/day to about 4 mg/kg/day. In one embodiment, clonidine is administered in an amount of about 0.01 mg/kg/day to about 0.4 mg/kg/day.

In various embodiments, there is a pharmaceutical formulation comprising: clonidine, wherein the clonidine comprises from about 0.1 wt. % to about 30 wt. % of the formulation or 1 wt. % to about 20 wt. % of the formulation, and at least one biodegradable polymer. In some embodiments, the pharmaceutical clonidine comprises from about 3 wt. % to about 20 wt. %, about 3 wt. % to about 18 wt. %, about 5 wt. % to about 15 wt. % or about 7.5 wt. % to about 12.5 wt. % of the formulation. By way of example, when using a 5%-15% clonidine composition, the mole ratio of clonidine to polymer would be from approximately 16-53 when using an approximately 80 kDalton polymer that has a 267 grams/mole ratio. By way of another example, when using a 5%-15% clonidine base in the composition, the mole ratio of clonidine base to polymer would be from approximately 18-61 with a mole mass of 230 g/mol.

In some embodiments, the drug depot comprises at least one biodegradable material at a wt. % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot and the remainder is active and/or inactive pharmaceutical ingredients.

In some embodiments, the at least one biodegradable polymer comprises poly(lactic-co-glycolide) (PLGA) or poly(orthoester) (POE) or a combination thereof. The poly(lactic-co-glycolide) may comprise a mixture of polyglycolide (PGA) and polylactide and in some embodiments, in the mixture, there is more polylactide than polyglycolide. In various embodiments, there is 100% polylactide and 0% polyglycolide; 95% polylactide and 5% polyglycolide; 90% polylactide and 0.10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80%, polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 26% polylactide; at least 15% polylactide; at least 10% polylactide; or at least 5% polylactide; and the remainder of the biopolymer is polyglycolide.

Additionally, by varying the comonomer ratio of the various monomers that form a polymer (e.g., the L/G/CL or G/CL ratio for a given polymer), there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L (CL refers to caprolactone, G refers to glycolic acid and L refers to lactic acid) with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery.

In various embodiments, the drug particle size used in the drug depot is from about 5 to 30 micrometers, however, in various embodiments ranges from about 1 micron to 250 microns may be used. In some embodiments, the biodegradable polymer comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation or at least 97 wt. % of the formulation. In some embodiments, the at least one biodegradable polymer and the clonidine are the only components of the pharmaceutical formulation.

In some embodiments, at least 75% of the particles have a size from about 1 micrometer to about 200 micrometers. In some embodiments, at least 85% of the particles have a size from about 10 micrometers to about 200 micrometers. In some embodiments, at least 95% of the particles have a size from about 10 micrometers to about 200 micrometers. In some embodiments, all of the particles have a size from about 10 micrometers to about 200 micrometers.

In some embodiments, at least 75% of the particles have a size from about 20 micrometers to about 180 micrometers. In some embodiments, at least 85% of the particles have a size from about 20 micrometers to about 180 micrometers. In some embodiments, at least 95% of the particles have a size from about 20 micrometers to about 180 micrometers. In some embodiments, all of the particles have a size from about 20 micrometers to about 180 micrometers.

In some embodiments, there is a pharmaceutical formulation in a drug, depot for preventing or reducing bleeding at a surgical site comprising: clonidine, wherein the clonidine is in the form of a hydrochloride salt, and comprises from about 0.1 wt. % to about 30 wt. %, and at least one biodegradable polymer, wherein the at least one biodegradable polymer comprises poly(lactide-co-glycolide) (or poly(lactic-co-glycolic acid)) or poly(orthoester) or a combination thereof, and said at least one biodegradable polymer comprises at least 70 wt. % of the formulation.

In some embodiments, there is a pharmaceutical formulation in a depot for preventing or reducing bleeding at a surgical site comprising clonidine, wherein the clonidine is in a mixture of clonidine hydrochloride and clonidine base and the mixture comprises from about 0.1 wt. % to about 30 wt. % of the formulation and a polymer comprises at least 70% of the formulation. In some embodiments, the polymer in this formulation is polyorthoester. Polyorthoester can be obtained from A.P. Pharma, Inc. (Redwood City, Calif.) or through the reaction of a bis(ketene acetal) such as 3,9-diethylidene-2,4,8,10-tetraoxospiro[5,5]undecane (DETOSU) with suitable combinations of diol(s) and/or polyol(s) such as 1,4-trans-cyclohexanedimethanol and 1,6-hexanediol or by any other chemical reaction that produces a polymer comprising orthoester moieties.

In some embodiments, there are methods for reducing, preventing or treating bleeding at a surgical site. These methods comprise: administering a pharmaceutical composition to a surgical site to reduce, present or treat bleeding, wherein said pharmaceutical composition comprises from about 1 wt. % to about 20 wt. % of the formulation and at least one biodegradable polymer. In some embodiments, the loading is from about 5 wt. % to about 10 wt. %. In some embodiments, the loading is from about 10 wt. % to about 20 wt. %. In some embodiments, there is a higher loading of clonidine, e.g., at least 20 wt. %, at least 30 wt. %, at least 40 wt. %, at least 50 wt. %, at least 60 wt. %, at least 70 wt. %, at least 80 wt. %, or at least 90 wt. %.

In some embodiments, the drug depot contains excipients along with the clonidine. Exemplary excipients that may be formulated with clonidine in addition to the biodegradable polymer include but are not limited to MgO (e.g., 1 wt. %), 5050 DLG 6E, 5050 DLG 1A, mPEG, TBO-Ac, mPEG, Span-65, Span-85, pluronic F127, TBO-Ac, sorbital, cyclodextrin, maltodextrin, pluronic F68, CaCl, 5050 DLG-7A and combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments; the excipients comprise from about 0.001 wt. % to about 50 wt. % of the formulation. In some embodiments, the excipients comprise from about 0.001 wt. % to about 2 wt. % of the formulation.

In various embodiments, the drug depot comprises from about 0.1% to 10% by weight clonidine, 75% to 94% by weight of a polymer and 5% to 15% by weight of an excipient. mPEG may be used as an excipient or plasticizer for a polymer as it imparts malleability to the resulting formulation. PEG 300 may also be used as an excipient. In addition, a combination of PEG 300 and NMP may be used as the excipient. The polymer may comprise PLGA.

A strategy of triangulation may be effective when administering these pharmaceutical formulations. Thus, a plurality (at least two, at least three, at least four, at least five, at least six, at least seven, etc.) of drug depots comprising the pharmaceutical formulations may be placed around the target tissue site (such as for example the surgical site that may be prone to bleeding) such that the target tissue site falls within a region that is either between the depots or formulations when there are two, or within an area whose perimeter is defined by a set of depots or formulations.

In some embodiments, the formulations are slightly rigid with varying length, widths, diameters, etc. For example, certain formulations may have a diameter of 0.50 mm and a length of 4 mm. It should be noted that particle size may be altered by techniques such as using a mortar and pestle, jet-drying or jet milling.

In some embodiments, clonidine is released at a rate of 2-3 µg per day for a period of at least three days. In some embodiments, this release rate continues for, at least four days, at least five days, at least six days, at least seven days, at least eight days, at least nine days, at least ten days, at least fifteen days, at least twenty-five days, at least fifty days, at least ninety days, at least one hundred days, at least one-hundred and thirty-five days, at least one-hundred and fifty days, or at least one hundred and eighty days. For some embodiments, 300-425 micrograms of clonidine as formulated with a biopolymer are implanted into a person at or near the surgical site. If clonidine is implanted at multiple sites that triangulate the target site, then in some embodiments, the total amount of clonidine at each site is a fraction of the total 300-425 micrograms. For example, one may implant a single dose of 324 micrograms at one site, or two separate doses of 162 micrograms at two sites, or three separate doses of 108 micrograms at three sites that triangulate the tissue site. It is important to limit the total dosage to an amount less than that which would be harmful to the patient. However, in some embodiments, although when there are a plurality of sites each site may contain less than the total dose that might have been administered in a single application, it is important to remember that each site will independently have a release profile, and the biopolymers' concentration and substance should be adjusted accordingly to ensure that the sustain release occurs over sufficient time.

Clonidine may also be administered with non-active ingredients. These non-active ingredients may have multi-functional purposes including the carrying, stabilizing and controlling the release of clonidine and/or additional therapeutic agents. The sustained release process, for example, may be by a solution-diffusion mechanism or it may be governed by an erosion-sustained process. Typically, the depot will be a solid or semi-solid formulation comprised of a biocompatible material that can be biodegradable. The term "solid" is intended to mean a rigid material, while "semi-solid" is intended to mean a material that has some degree of flexibility, thereby allowing the depot to bend and conform to the surrounding tissue requirements.

In various embodiments, the non-active ingredients will be durable within the surgical site for a period of time equal to or greater than (for biodegradable components) or greater than (for non-biodegradable components) the planned period of drug delivery.

In some embodiments, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

The depot may contain non-active materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such non-active materials will be present within the range of 0-75 wt %, and more typically within the range of 0-30 wt %. In various embodiments, the non-active ingredients (such as surfactants, excipients, buffering agents, pH adjusting agents, etc.) may comprise less than 50 wt. %, less than 40 wt. %, less than 30 wt. %, less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. % of the drug depot.

The depot can be different sizes, shapes and configurations. There are several factors that can be taken into consideration in determining the size, shape and configuration of the drug depot. For example, both the size and shape may allow for ease in positioning the drug depot at the target tissue site. In addition, the shape and size of the system should be selected so as to minimize or prevent the drug depot from moving after implantation or injection. In various embodiments, the drug depot can be shaped like a pellet, a sphere, a cylinder such as a rod or fiber, a flat surface such as a disc, film or sheet or the like. Flexibility may be a consideration so as to facilitate placement of the drug depot. In various embodiments, the drug depot can be different sizes, for example, the drug depot may have a length of from about 0.5 mm to 5 mm and a diameter of from about 0.01 to about 4 mm. In various embodiments, the drug depot may have a layer thickness of from about 0.005 to 1.0 mm or from 0.05 to 0.75 mm. In various embodiments, the drug depot is coated on a medical device and clonidine is released therefrom.

Radiographic markers can be included on or in the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, bismuth, tantalum, tungsten, iodine, calcium phosphate, and/or metal beads or particles. In various embodiments, the radiographic marker could be a spherical shape or a ring around the depot.

Gel

In various embodiments, the depot is in the form of a gel and the gel has a pre-dosed viscosity in the range of about 1 to about 500 centipoise (cps), 1 to about 2000 cps, or 1 to about 200 cps, or 1 to about 100 cps. After the gel is administered to the target site or in or on the medical device, the viscosity of the gel will increase and the gel will have a modulus of elasticity (Young's modulus) in the range of about $1\times10^2$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In one embodiment, a depot is provided that contains an adherent gel comprising at least clonidine that is evenly distributed throughout the gel. The gel may be of any suitable type, as previously indicated, and should be sufficiently viscous so as to prevent the gel from migrating from the surgical site once deployed; the gel should, in effect, "stick" or adhere to the targeted tissue site. The gel may, for example, solidify upon contact with the targeted tissue or after deployment from a targeted delivery system thereby preventing bleeding. The targeted delivery system may be, for example, a syringe, a catheter, needle or cannula or any other suitable device. The targeted delivery system may inject the gel into or on the targeted site. The therapeutic agent may be mixed into the gel prior to the gel being deployed at the targeted site. In various embodiments, the gel may be part of a two-component delivery system and when the two/components are mixed, a chemical process is activated to form the gel and cause it to stick or to adhere to the target site.

In various embodiments, a gel is provided that hardens or stiffens after delivery thereby preventing or reducing bleeding at the site of delivery. Typically, hardening gel formulations may have a pre-dosed modulus of elasticity in the range of about $1\times10^2$ to about $3\times10^5$ dynes/cm$^2$, or $2\times10^4$ to about $2\times10^5$ dynes/cm$^2$, or $5\times10^4$ to about $1\times10^5$ dynes/cm$^2$. The post-dosed hardening gels (after delivery) may have a rubbery consistency and have a modulus of elasticity in the range of about $1\times10^4$ to about $2\times10^6$ dynes/cm$^2$, or $1\times10^5$ to about $7\times10^5$ dynes/cm$^2$, or $2\times10^5$ to about $5\times10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone) while bleeding at the site is prevented or reduced.

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances.

In various embodiments, the molecular weight of the gel can be varied by any one of the many methods known in the art. The choice of method to vary molecular weight is typically determined by the composition of the gel (e.g., polymer versus non-polymer). For example, in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, incorporation of chain transfer or chain capping agents and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which include a low-molecular weight polymer.

When the gel is designed to be a flowable gel, it can vary from low viscosity, similar to that of water, to a high viscosity, similar to that of a paste, depending on the molecular weight and concentration of the polymer used in the gel. The viscosity of the gel can be varied such that the polymeric composition can be applied to a patient's tissues by any convenient technique, for example, by brushing, spraying, dripping, injecting or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and may have a longer degradation time). Typically, a gel with a high molecular weight provides a stronger matrix and the matrix takes more time to degrade. In contrast, a gel with a low molecular weight degrades more quickly and provides a softer matrix. This will happen when the polymers used have the same chemistry (low MW DL and high MW DL). In various embodiments, the gel has a molecular weight, as shown by the inherent viscosity, from about 0.10 dL/g to about 1.2 dL/g or from about 0.10 dL/g to about 0.40 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof. Carbopol, poly-(hydroxyethylmethacrylate), poly-(methoxyethylmethacrylate), poly(methoxyethoxyethyl methacrylate), polymethylmethacrylate (PMMA), methylmethacrylate (MMA), gelatin, polyvinyl alcohols, propylene glycol, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, when a polymer is employed in the gel, the polymeric composition includes about 10 wt % to about 90 wt % or about 30 wt % to about 60 wt % of the polymer.

In various embodiments, the gel is a hydrogel made of high molecular weight biocompatible elastomeric polymers of synthetic or natural origin. A desirable property for the hydrogel to have is the ability to respond rapidly to bleeding as well as mechanical stresses, particularly shears and loads, at the surgical site.

Hydrogels obtained from natural sources are particularly appealing because they are more likely to be biocompatible for in vivo applications. Suitable hydrogels include natural hydrogels, such as, for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to, those formed from polyvinyl alcohol, acrylamides such as polyacrylic acid and poly(acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly (N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane or a combination thereof.

In various embodiments, rather than directly admixing the therapeutic agents into the gel, microspheres may be dispersed within the gel, the microspheres being loaded with at least one analgesic agent and/or at least one anti-inflammatory agent. In one embodiment, the microspheres provide for a sustained release of at least clonidine. In yet another embodiment, the gel, which is biodegradable, prevents the microspheres from releasing clonidine; the microspheres thus do not release clonidine until it has been released from the gel. For example, a gel may be deployed around a target tissue site (e.g., a surgical site likely to have bleeding or one where there is already bleeding). Dispersed within the gel is a plurality of microspheres that encapsulate clonidine. Certain of these microspheres degrade once released from the gel, thus releasing clonidine. Clonidine may be placed into separate microspheres and then the microspheres combined, or the active can first be combined and then placed into the microspheres together.

Microspheres, much like a fluid, may disperse relatively quickly, depending upon the surrounding tissue type, and hence disperse the at least one analgesic agent and at least one anti-inflammatory agent. In some embodiments, the diameter of the microspheres range from about 10 microns in diameter to about 200 microns in diameter. In some embodiments, they range from about 20 to 120 microns in diameters. Methods for making microspheres include but are not limited to solvent evaporation, phase separation and fluidized bed coating.

The present invention also contemplates, the use of adherent gels to so constrain dispersal of the therapeutic agent. These gels may be deployed, for example, in a disc space, in a spinal canal or in surrounding tissue.

Cannulas and Needles

It will be appreciated by those with skill in the art that the depot dependent upon its form can be administered to the surgical site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments, the gauge of the needle or cannula is about 18 to about 22 gauge.

In various embodiments, like a pellet and/or gel, the cannula or needle includes dose radiographic markers that indicate location at or near the site beneath the skin, so that the user may accurately position the depot at or near the site. Examples of such radiographic markers include, but are not limited to, barium, bismuth, tantalum, tungsten, iodine, calcium phosphate, and/or metal beads or particles.

Sterilization

The drug depot and/or medical device may be sterilizable. In various embodiments, one or more components of the drug depot and/or medical device are sterilized by radiation in a terminal sterilization step in the final packaging. Terminal sterilization of a product provides greater assurance of sterility than from processes such as an aseptic process, which requires individual product components to be sterilized separately and the final package to be assembled in a sterile environment.

Typically, in various embodiments, gamma radiation is used in the terminal sterilization step which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

Kits

In various embodiments, a kit is provided that may include additional parts along with the drug depot combined together to be used to implant the drug depot (e.g., strip). The kit may include the drug, depot in a first compartment. The second compartment may include instruments needed for the localized drug delivery. A third compartment may include gloves, drapes, wound dressings and other procedural supplies for maintaining sterility of the implanting process as well as an instruction booklet. A fourth compartment may include additional cannulas and/or needles. A fifth compartment may include the agent for radiographic imaging. Each tool may be separately packaged in a plastic pouch that is radiation sterilized. A cover of the kit may include illustrations of the implanting procedure and a clear plastic cover may be placed over the compartments to maintain sterility.

Administration

In various embodiments, clonidine may be parenterally administered. The term "parenteral" as used herein refers to modes of administration, which bypass the gastrointestinal tract, and include for example, localized intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof.

Parenteral administration may additionally include, for example, an infusion pump that locally administers a pharmaceutical composition (e.g., clonidine) through a catheter near the spine or one or more inflamed joints, an implantable mini-pump that can be inserted at or near the target site, an implantable controlled release device or sustained release delivery system that can release a certain amount of the composition continuously per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times or at set intervals between deliveries.

Potential drug delivery devices suitable for adaptation for the methods described herein include but are not limited to those described, for example, in U.S. Pat. No. 6,551,290 (assigned to Medtronic, the entire disclosure is herein incorporated by reference), which describes a medical catheter for target specific drug delivery; U.S. Pat. No. 6,571,125 (assigned to Medtronic, the entire disclosure is herein incorporated by reference), which describes an implantable medical device for controllably releasing a biologically active agent; U.S. Pat. No. 6,594,880 (assigned to Medtronic, the entire disclosure is herein incorporated by reference), which describes an intraparenchymal infusion catheter system for delivering therapeutic agents to selected sites in an organism; and U.S. Pat. No. 5,752,930 (assigned to Medtronic, the entire disclosure is herein incorporated by reference), which describes an implantable catheter for infusing equal volumes of agents to spaced sites. In various embodiments, pumps may be adapted with a pre-programmable implantable apparatus with a feedback regulated delivery, a micro-reservoir osmotic release system for controlled release of chemicals, small, light-weight devices for delivering liquid medication, implantable microminiature infusion devices, implantable ceramic valve pump assemblies, or implantable infusion pumps with a collapsible fluid chamber. Alzet® osmotic pumps (Durect Corporation, Cupertino, Calif.) are also available in a variety of sizes, pumping rates and durations suitable for use in the described methods.

In some embodiments, the method of the present application comprises inserting a cannula at or near a target tissue site and implanting the drug depot at the target site beneath the skin of the patient and brushing, dripping, spraying, injecting, or painting the gel in the target site to hold or have the drug depot adhere to the target site. In this way, unwanted migration of the drug depot away from the target site is reduced or eliminated.

In various embodiments, because clonidine is locally administered, therapeutically effective doses may be less than doses administered by other routes (oral, topical, etc.). For example, the drug dose delivered from the drug depot may be, for example, 10%, 20%, 30%, 40%, 50%, 60%, 70%, 80%, 90%, 95%, 99%, or 99.9% less than the oral dosage or injectable dose. In turn, systemic side effects, such as for example, liver transaminase elevations, hepatitis, liver failure, myopathy, constipation, etc. may be reduced or eliminated.

In various embodiments, to administer the gel having the drug depot dispersed therein to the desired site, first the cannula or needle can be inserted at the target site and the gel administered (e.g., brushed, dripped, injected, or painted, etc.) at or near the target site. In those embodiments where the drug depot is separate from the gel, first the cannula or needle can be inserted at the target site of injection and one or more base layer(s) of gel can be administered to the target site. Following administration of the one or more base layer(s), the drug depot can be implanted on or in the base layer(s) so that the gel can hold the depot in place or reduce migration. If required, a subsequent layer or layers of gel can be applied on the drug depot to surround the depot and further hold it in place. Alternatively, the drug depot may be implanted first and then the gel placed (e.g., brushed, dripped, injected, or painted, etc.) around the drug depot to hold it in place. By using the gel, accurate and precise implantation of a drug depot can be accomplished with minimal physical and psychological trauma to the patient. The gel also avoids the need to suture the drug depot to the target site reducing physical and psychological trauma to the patient.

FIG. 1 illustrates a number of common locations within a patient that may be sites at which surgery can occur and therefore bleeding can develop during or after surgery. It will be recognized that the locations illustrated in FIG. 1 are merely exemplary of the many different locations within a patient that may be the sites where bleeding may occur during or after surgery. For example, bleeding may occur at a patient's knees 21, hips 22, fingers 23, thumbs 24, neck 25 and spine 26.

Figure 2:
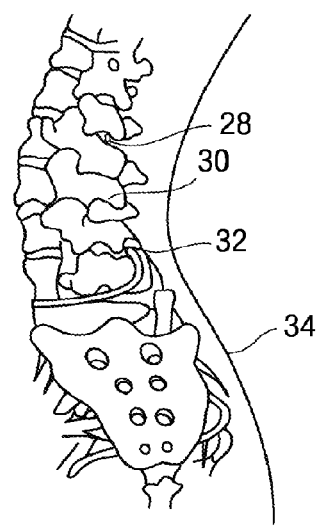
FIG. 2 illustrates a schematic dorsal view of the spine and sites at which a drug depot or the medical device containing clonidine can locally be administered thereto to prevent, reduce and/or treat bleeding.

One exemplary embodiment where the depot is suitable for use in preventing bleeding is illustrated in FIG. 2. Schematically shown in FIG. 2 is a dorsal view of the spine 30 and sites where the drug depot or medical device containing the drug depot may be implanted, injection, sprayed, brushed, inserted using a cannula or needle, etc. (e.g., spinal disc space, spinal canal, soft tissue surrounding the spine, nerve root, etc.). In FIG. 2, one or more drug depots 28 and 32 are delivered to various sites along the spine. In this way, when several drug depots are to be implanted, they are implanted in a manner that optimizes location, accurate spacing, and drug distribution.

Although the spinal site is shown, as described above, the drug depot can be delivered to any surgical site beneath the skin, including but not limited to, a site comprising at least one muscle, ligament, tendon or cartilage; a foot; a finger; a toe; a hand; a wrist; gums; the jaw; a knee joint; a spinal disc; the spinal foraminal space; and a site near the spinal nerve root or spinal canal.

In some embodiments, the drug depot may release 5%, 10%, 15%, 20%, 25%, 30%, 40%, 50%, 60%, 70%, 80%, 90%, 95%, or 99% of the clonidine or pharmaceutically acceptable salt thereof relative to a total amount of clonidine loaded in the drug depot over a period of 3 to 12 days, 5 to 10 days or 7 to 10 days, 7 to 30 days or 7 to 60 days after the drug depot is administered to the target site.

In some embodiments, the drug depot may release about 20% to about 99% of the clonidine or pharmaceutically acceptable salt thereof relative to a total amount of clonidine loaded in the drug depot over a period of 3 to 7 days after the drug depot is administered to the surgical site.

In some embodiments, an implantable medical device is provided having an alpha adrenergic agonist disposed on all or a portion of the medical device. The surgeon will implant the device at the target tissue site, such as for example, a spinal foraminal space, and the risk of bleeding developing may be reduced as the alpha adrenergic agonist is released from the medical device. The alpha adrenergic agonist will cause vasoconstriction at the target site confining any existing bleeding to the area, where it can be removed by the body itself. Sometimes after surgery, a seroma or a pocket of serous fluid will form. This is particularly so when small blood vessels are ruptured during surgery where blood plasma can seep out. Inflammation caused by dying injured cells also contributes to the fluid. By using an alpha adrenergic agonist that has delayed release properties, the area surrounding the surgical site undergoes vasoconstriction and thus formation of a seroma at or near the surgical site is reduced or prevented.

Method of Making

In various embodiments, the drug depot comprising the active ingredients (e.g., clonidine) can be made by combining a biocompatible polymer and a therapeutically effective amount of the active ingredients or pharmaceutically acceptable salts thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise one or more of the following: other therapeutic agent(s) and other optional additives such as radiographic agent(s), etc., in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the active ingredients (e.g., alpha agonist), optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, certain therapeutic agents may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding the biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, rosy kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with the therapeutic agent (e.g., clonidine) under conditions of lower temperature and mechanical shear, and the resulting mixture is shaped into the active ingredient containing drug depot. Conversely, in another embodiment, the biocompatible polymer can be pre-compounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of certain active ingredients, such as an anti-inflammatory and analgesic (e.g., clonidine) because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form at a reduced temperature under shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet, strip, etc.) is cooled. Examples of cooling processes include air cooling and/or immersion in a cooling bath. In some embodiments, a water bath is used to cool the extruded depot. However, where a water-soluble therapeutic agent such as an active ingredient is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape or disposing it on or in a medical device. In various embodiments, active ingredients are used and mixed or sprayed with the PLGA or PEG550 polymer, and the resulting depot may be formed by extrusion and dried.

Having now generally described the invention, the same may be more readily understood through the following reference to the following examples, which are provided by way of illustration and are not intended to limit the present invention unless specified.

EXAMPLES

Example 1

Depots or implants comprising clonidine were prepared according to the following procedures:

Materials: Poly(D,L-lactide-co-glycolide) having a 50:50 lactide to glycolide molar ratio (PLGA50501A), a molecular weight of 8 kDa, an intrinsic viscosity of 0.12 dL/g and acid end capped polymer chain ends was purchased from Lakeshore Biomaterials (Birmingham, Ala.). Clonidine HCl was purchased from Spectrum Chemicals (Gardena, Calif.). Methoxy polyethylene glycol (mPEG) having an average molecular weight of 550 was purchased from Sigma-Aldrich. Methanol and acetone were also purchased from Sigma-Aldrich.

Methods:

Preparation of Spray-Dried Clonidine HCl: Clonidine HCl was dissolved in methanol to yield a 12% (w/w) solution. The solution was spray-dried in a Buchi B-290 Mini Spray Dryer (Buchi Laboratorium AG, Switzerland) using a 120 kHz Sono-Tek ultrasonic nozzle (Sono-Tek Corp., Milton, N.Y). The processing parameters were set as follows: inlet temp. (70° C.), aspirator (80%), nitrogen inlet (50 mm), spray flow rate (80 mL/hr) and ultrasonic generator (0.8 watts). The spray-dried powder was collected and dried for an additional 24 hours at 70° C. and 15 mmHg vacuum.

Preparation of Melt Extruded Rods: Two formulations were prepared for melt extrusion. Both formulations contained PLGA50501A ground into powder using a Retsch (Retsch GmbH, Germany) rotor mill with an 80 micrometer sieve filter. The first such formulation contained 85% (w/w) ground PLGA50501A, 5% (w/w) spray-dried clonidine HCl, and 10% (w/w) mPEG. The second formulation contained 87.5% (w/w) ground PLGA50501A, 2.5% (w/w) spray-dried clonidine HCl, and 10% (w/w) mPEG. Both formulations were dry mixed with a spatula prior to being fed into a Haake Mini-Lab twin screw extruder (Thermo Fischer Scientific, Waltham, Mass.). The extruder settings were as follows: 70° C. and 30 RPM for the 2.5% and 5% clonidine formulations. Both formulations were extruded out of a 1.5 mm diameter dye.

Strip Preparation: Extruded formulations were pressed into sheets of a desired thickness using a Carver Laboratory Heat Press (Carver, Inc., Wabash, Ind.) set at 50° C. The sheets were cut by razor blades to form strips or ribbons of the desired dimensions. The dimensions of the strips or ribbons were as follows (L×W×H which is length by width by height): the strips or ribbons comprising the 2.5% clonidine formulation were 9 mm×1.5 mm×0.5 mm, and the strips or ribbons comprising the 5.0% clonidine formulation were 9 mm×1.5 mm×0.5 mm. It should be noted that the size of the strips or ribbons was selected for a rat paw implant.

Figure 3:
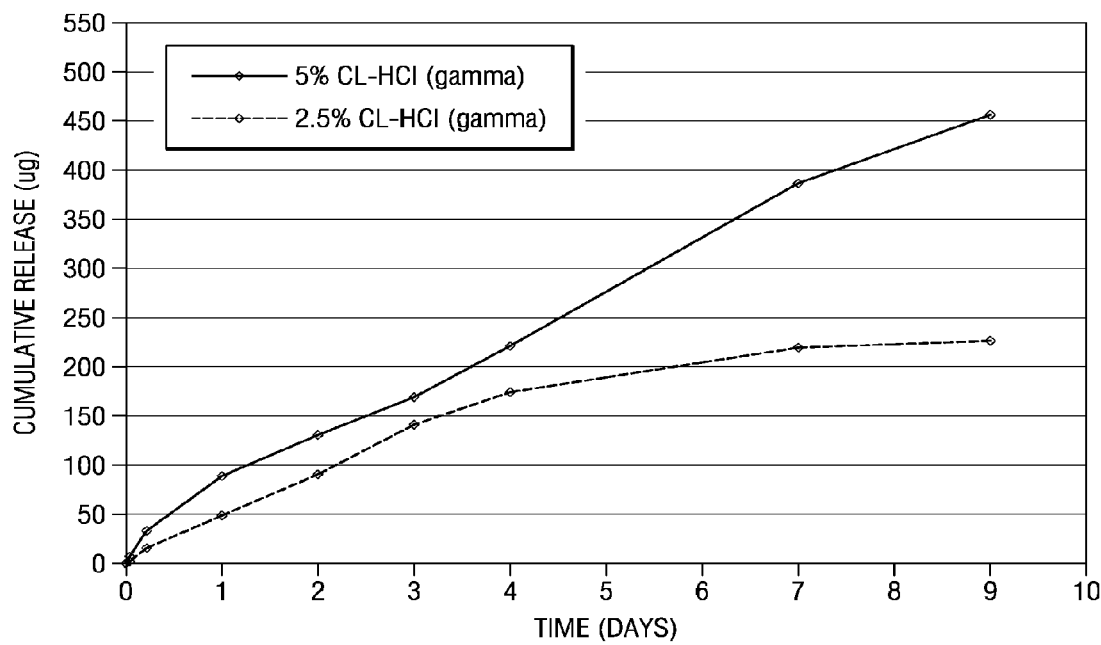
FIG. 3 is a graphic representation of a study of the average cumulative release in ug of clonidine for clonidine strip depots described in Example 1.
Figure 4:
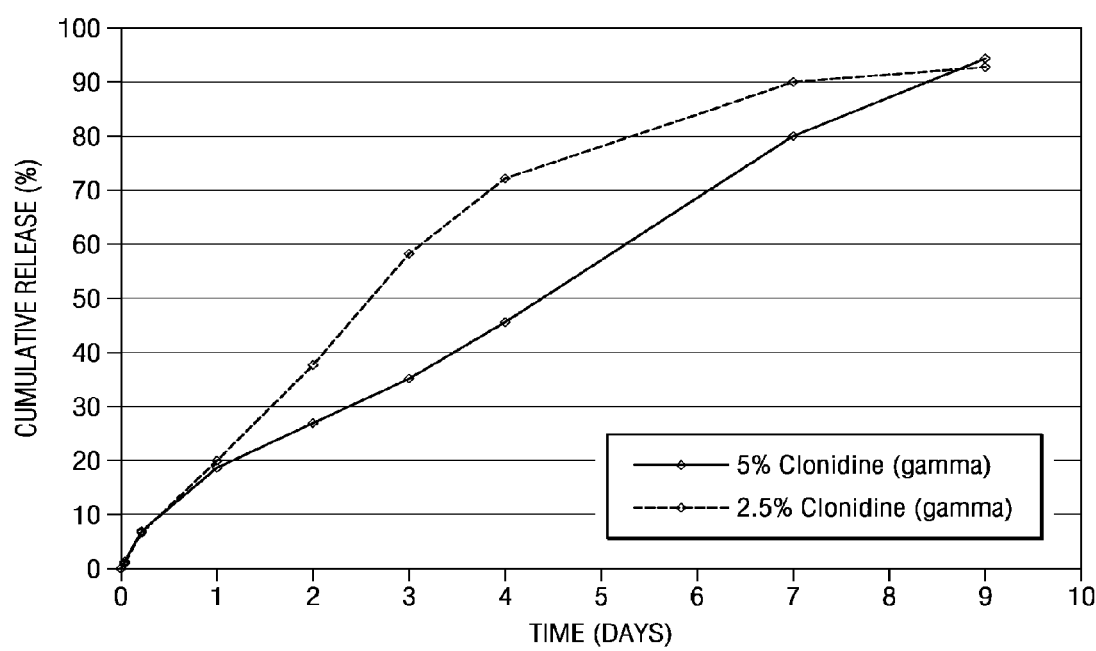
FIG. 4 is a graphic representation of a study of the average percentage cumulative release of clonidine for clonidine strip depots described in Example 1.

In Vitro Drug Elution Testing: Each strip or ribbon depot or implant was tested in triplicate and placed in 20 mL scintillation vials for drug elution testing. The 5% clonidine and 2.5% clonidine strips or ribbons were incubated in 5 mL of phosphate buffered saline pH 7.4 (Hyclone) at 37° C. under mild agitation. At pre-selected time points, the buffer was removed for analysis and replaced with fresh buffer medium. The drug content was quantified at 226 nm for clonidine by a Molecular Devices SpectraMax M2 (Sunnyvale, Calif.) plate reader. FIGS. 3 and 4 show the average release rate of clonidine in micrograms and percentages for strip or ribbon depots. In particular, in FIG. 3, the 5% clonidine strips released faster (over 450 mcg in 9 days) than the 2.5% clonidine strips (over 200 mcg over 9 days). From FIG. 3, it is apparent that the more wt. % drug load, the greater the release of drug. In FIG. 4, the 2.5% clonidine strips released faster than the 5% clonidine strips, however, the 5% clonidine strips had a steadier release than the 2.5% clonidine strips. Table 1 below summarizes the elution profile for the 5% clonidine and 2.5% clonidine strips.

In vivo data: These depots of clonidine were tested in Brennan rats to determine their in vivo performance. The results are summarized below in Table 1:

TABLE 1

| Depot Number | Polymer (wt. %) | Active wt. % of Clonidine | Excipient (wt. %) | Handling Property | In vitro elution profile | In vivo data |
|---|---|---|---|---|---|---|
| clonidine 1 | 85% PLGA 5050 1A | 5% (clonidine HCl) | 10% mPEG | Malleable | Day 1 release of 18%; by Day 9, 100% release | Statistically significant reduction in mechanical hyperalgesia on Days 2 and 3 |

TABLE 1-continued

| Depot Number | Polymer (wt. %) | Active wt. % of Clonidine | Excipient (wt. %) | Handling Property | In vitro elution profile | In vivo data |
|---|---|---|---|---|---|---|
| clonidine 2 | 85% PLGA 5050 1A | 2.5 % (clonidine HCl) | 10% mPEG | Malleable | Day 1 release of 22%; by Day 9, 100% release | Statistically significant reduction in mechanical hyperalgesia on Days 2-4 |

For all of the clonidine 1 and 2 depots, the polymer degraded in less than one month and the handling was of a malleable and formable product that could be extruded to a strip or ribbon-like dosage form. The efficacy of the clonidine 1 and 2 depot formulations was tested in the Brennan rat model of post-incisional pain. Mechanical hyperalgesia was used as the behavioral endpoint to assess the presence/absence of pain in the animal model following treatment with these drug formulations. Clonidine 1 depots showed statistically significant reduction in mechanical hyperalgesia on days 2 and 3 following administration compared to Brennan rats receiving no treatment. Clonidine 2 implants, though, showed statistical reversal in mechanical hyperlagesia on days 2, 3, and 4. This preliminary in vivo study has demonstrated both clonidine 1 and 2 implant formulations are effective in treating post-incisional pain in the Brennan rat as assessed by rats' behavioral response to mechanical stimuli following treatment with the clonidine implants.

Example 2

A number of strip or ribbon depots or implants comprising clonidine were prepared in which the polymer type, drug load and excipient (including some formulations in which there was no excipient) were varied. Representative formulations for the strip or ribbon depots are described below in Table 2. A number of tests were performed on these strip or ribbon depots, including in vitro release tests in which the number of micrograms released was measured, as well as the cumulative percentage release of clonidine. The results of these tests appear in FIGS. 5-12.

Materials: Poly(D,L-lactide-co-glycolide) having a 50:50 lactide to glycolide molar ratio having a molecular weight of 18 kDa, an inherent viscosity of 0.2 dL/g and acid end capped polymer chain ends (5050DLG 2A) was purchased from Lakeshore Biomaterials (Birmingham, Ala.). Poly(D,L-lactide-co-caprolactone) having a 10:90 lactide to caprolactone molar ratio, a molecular weight of 149 kDa, an inherent viscosity of 1.0 dL/g and acid end capped polymer chain ends (1090 DLCL 10A) was purchased from Lakeshore Biomaterials (Birmingham, Ala.). Poly(D,L-lactide-co-caprolactone) having a 65:35 lactide to caprolactone molar ratio, a molecular weight of 51 kDa, an inherent viscosity of 0.4 dL/g and acid end capped polymer chain ends (6535 DLCL 4A) was purchased from Lakeshore Biomaterials (Birmingham, Ala.). Poly(D,L-lactide-co-caprolactone) having a 25:75 lactide to caprolactone molar ratio, a molecular weight of 62 kDa, an inherent viscosity of 0.5 dL/g and acid end capped polymer chain ends (2575 DLCL 5A) was purchased from Lakeshore Biomaterials (Birmingham, Ala.). Clonidine HCl was purchased from Spectrum Chemicals (Gardena, Calif.). Pluronic F127 which is a nonionic surfactant, polyoxyethylene polyoxypropylene block copolymer (also known as Poloxamer 407) was purchased from BASF. Methanol and acetone were also purchased from Sigma-Aldrich.

Method of Preparation of Strip Depots: Several formulations were made according to the following method and the composition of these formulations is provided in Table 2 below associated with a batch number. For each formulation, the polymer, clonidine, and excipient (where included) were weighed into a glass lyophilization bottle. Glacial acetic acid was added to the bottle and sonicated for approximately 45 minutes to dissolve all of the components (approximately 5 grams of solids per 80 mL of acetic acid). The solution was then shell-frozen in an isopropyl alcohol/dry ice bath. The frozen material was then lyophilized for 24-72 hours to remove the glacial acetic acid. The resulting bulk material intermediate was then pressed into a thin film or sheet using a Carver Laboratory Heat Press (Carver, Inc., Wabash, Ind.). The film or sheet was prepared using a 0.25 mm shim at 65° C. and pressed for 1 minute at 5000 psi pressure. The sheet for each formulation was cut by razor blades to form strips or ribbons of a desired dimension. The dimensions of all of the strips or ribbons was 10 mm in length by 2 mm in width by 0.4 mm thick which was sized for a rat paw. The composition of the formulation used to make strips or ribbons is provided below in Table 2 associated with a batch number and the average amount of clonidine released daily by strips or ribbons made from each formulation is provided in Table 2 below.

TABLE 2

| Batch Number for Strips or Ribbons | Clonidine (wt. %) | 5050 DLG 2A (wt. %) | 1090 DL-CL 10A (wt. %) | 6535 DL-CL 4A (wt. %) | 2575 DL-CL 5A (wt. %) | Excipient (Pluronic F127) (wt. %) | Amount of Release of Clonidine for Day 1 (μg) | Amount of Daily Release of Clonidine for Days 2-10 (μg) |
|---|---|---|---|---|---|---|---|---|
| 00268-15 | 5 | — | 95 | — | — | — | 60 | 30-80 |
| 00268-22 | 5 | 15 | — | 75 | — | 5 | 25 | 10-80 |
| 00268-23 | 5 | 15 | — | — | 75 | 5 | 130 | 40-5 |
| 00268-24 | 2.5 | 16 | — | 38 | 38 | 5 | 35 | 30-50 |
| 00268-31 | 5 | — | 47.5 | 47.5 | — | — | 45 | 15-20 |
| 00268-32 | 5 | 25 | — | 60 | — | 5 | 30 | 20-70 |
| 00268-33 | 7 | 14.7 | — | 73.4 | — | 4.9 | 40 | 120-50 |
| 00268-34 | 5 | 15 | — | 60 | 20 | — | 15 | 5-20 |

TABLE 2-continued

| Batch Number for Strips or Ribbons | Clonidine (wt. %) | 5050 DLG 2A (wt. %) | 1090 DL-CL 10A (wt. %) | 6535 DL-CL 4A (wt. %) | 2575 DL-CL 5A (wt. %) | Excipient (Pluronic F127) (wt. %) | Amount of Release of Clonidine for Day 1 (µg) | Amount of Daily Release of Clonidine for Days 2-10 (µg) |
|---|---|---|---|---|---|---|---|---|
| 00268-35 | 1 | 20 | — | 37.1 | 37.1 | 4.8 | 10 | 10-20 |
| 00268-36 | 2.5 | 25.5 | — | 33.5 | 33.5 | 5 | 25 | 20-40 |

The handling properties of strips or ribbons from the batch numbers identified in Table 2 were noted. In particular, the strips or ribbons of batch numbers 00268-15, 00268-22, 00268-23 and 00268-24 were all found to be very flexible. Strips of batch number 00268-15 were firm, strips of batch number 00268-22 were soft and strips of batch numbers 00268-23 and 00268-24 were sticky. The strips of batch numbers 00268-31, 00268-32, 00268-33, 00268-34 and 00268-35 were all found to be very flexible.

Figure 5:
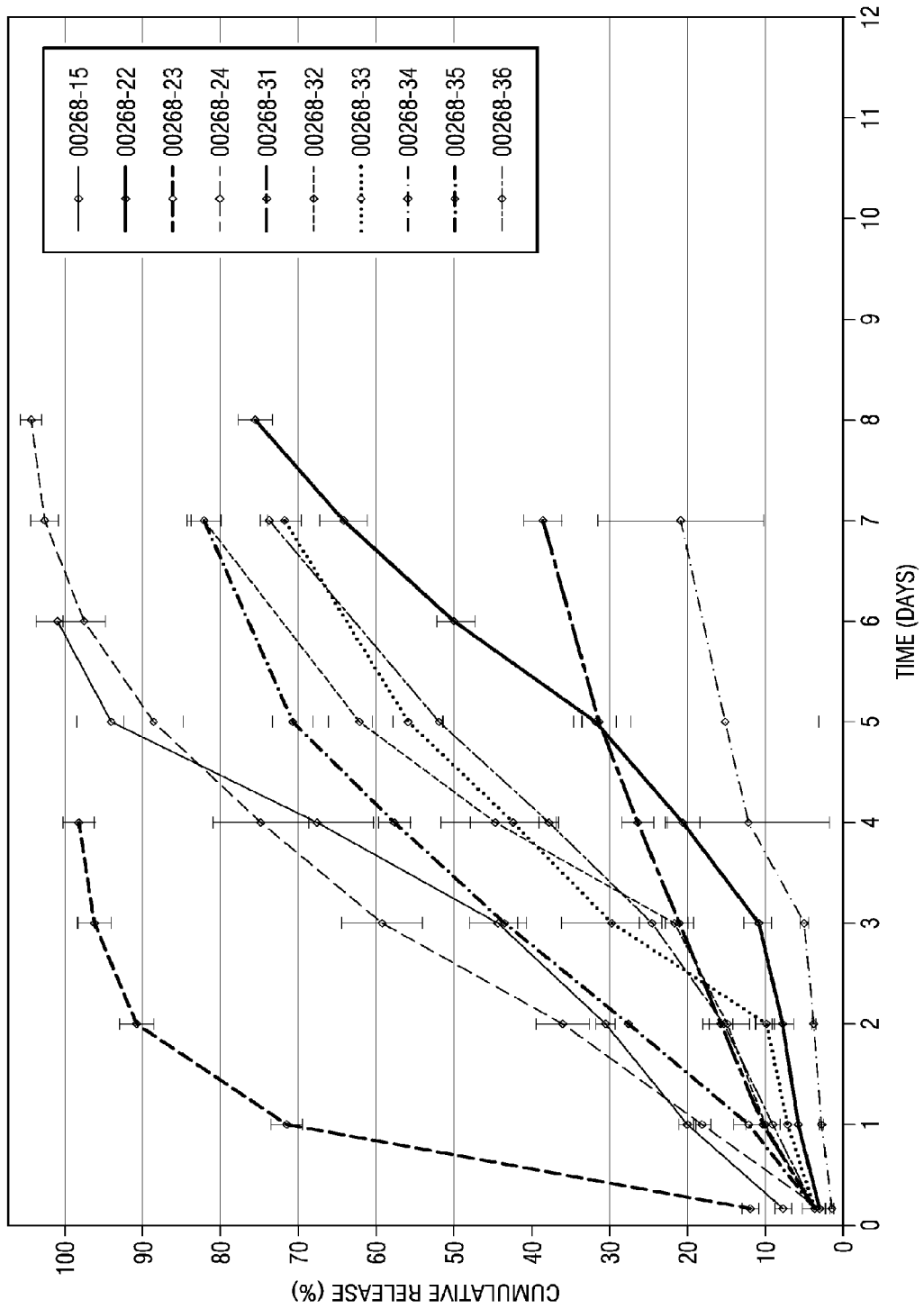
FIG. 5 is a graphic representation of the average percentage cumulative release of clonidine for several irradiated clonidine HCl strip or ribbon depots from Example 2 during days 1-8.
Figure 6:
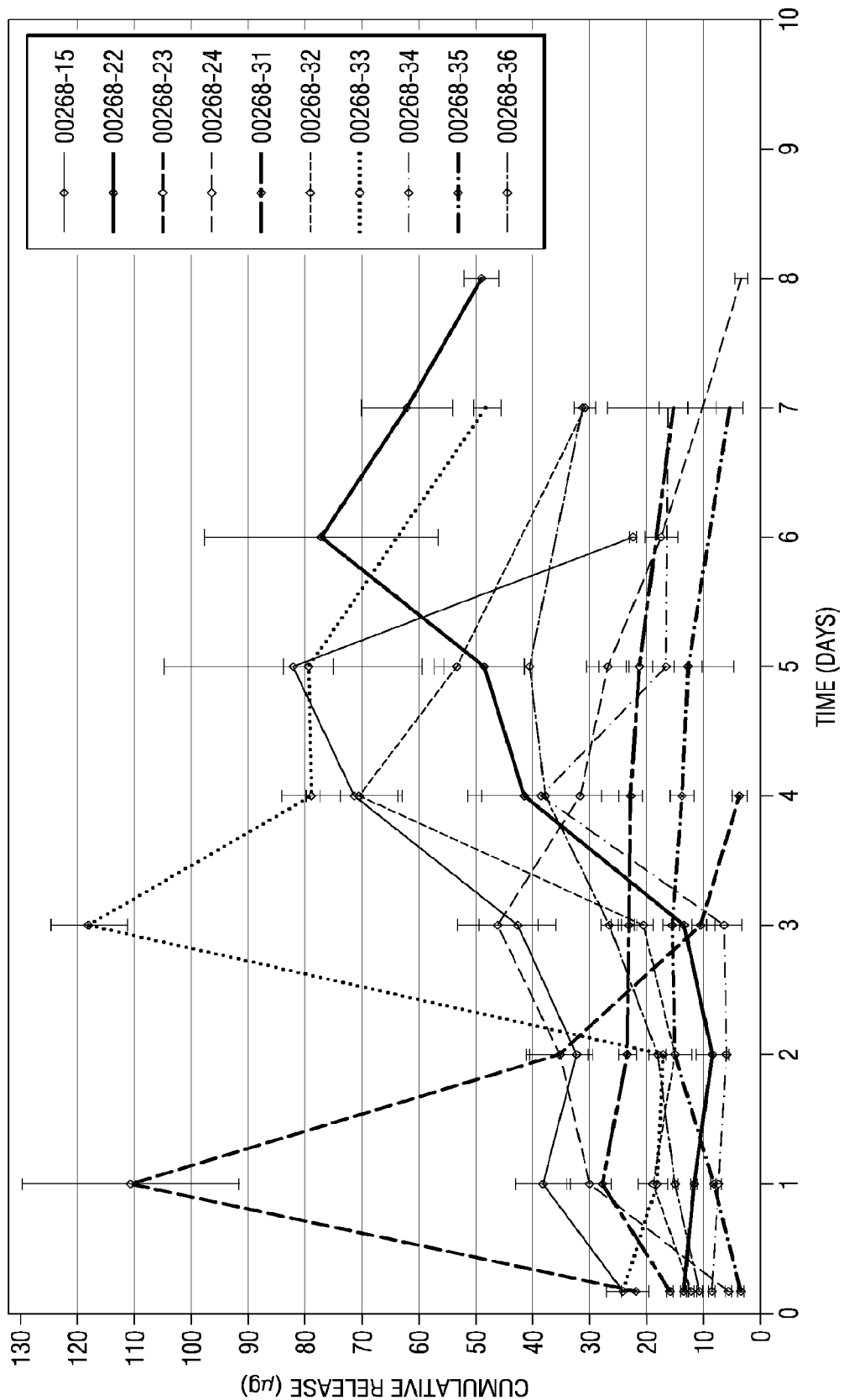
FIG. 6 is a graphic representation of the calculated average daily release of clonidine in micrograms during days 1-8 for the clonidine HCl strip or ribbon depots from Example 2.
Figure 7:
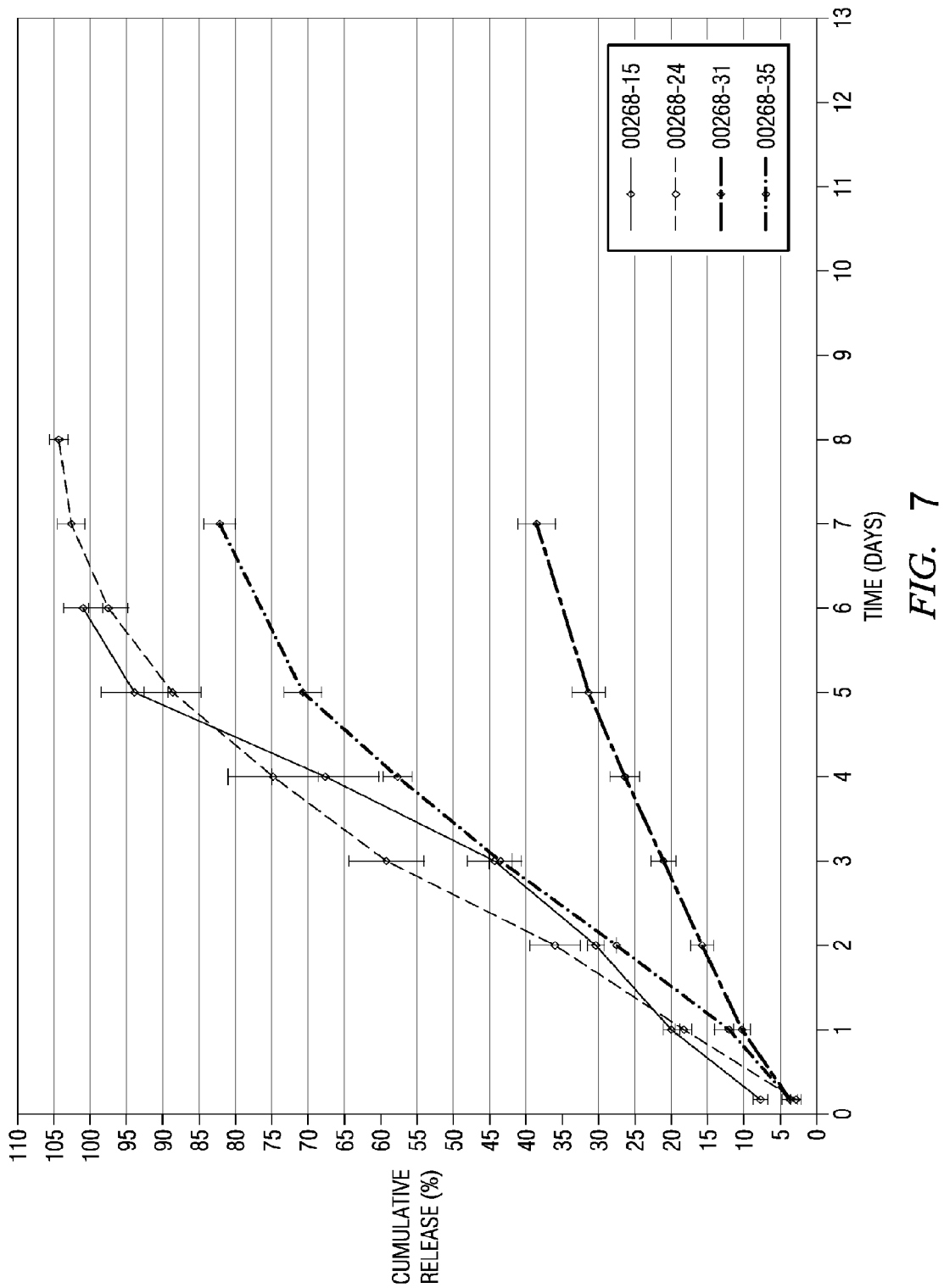
FIG. 7 is a graphic representation of the average percentage cumulative release of clonidine for certain clonidine HCl strip or ribbon depots illustrated in FIG. 5.
Figure 8:
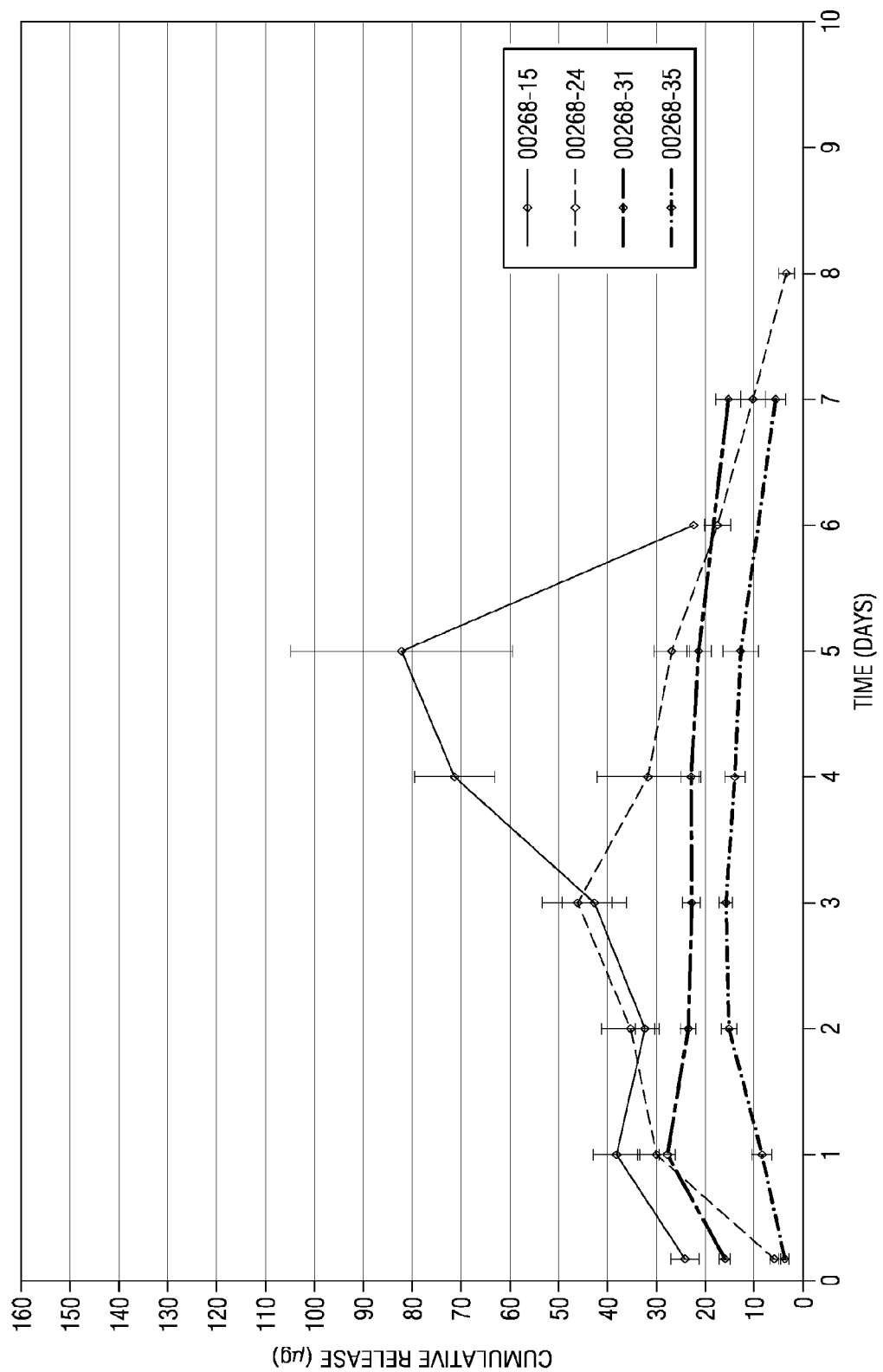
FIG. 8 is a graphic representation of the average daily release of clonidine in micrograms during days 1-8 for the certain clonidine HCl strip or ribbon depots illustrated in FIG. 7.
Figure 9:
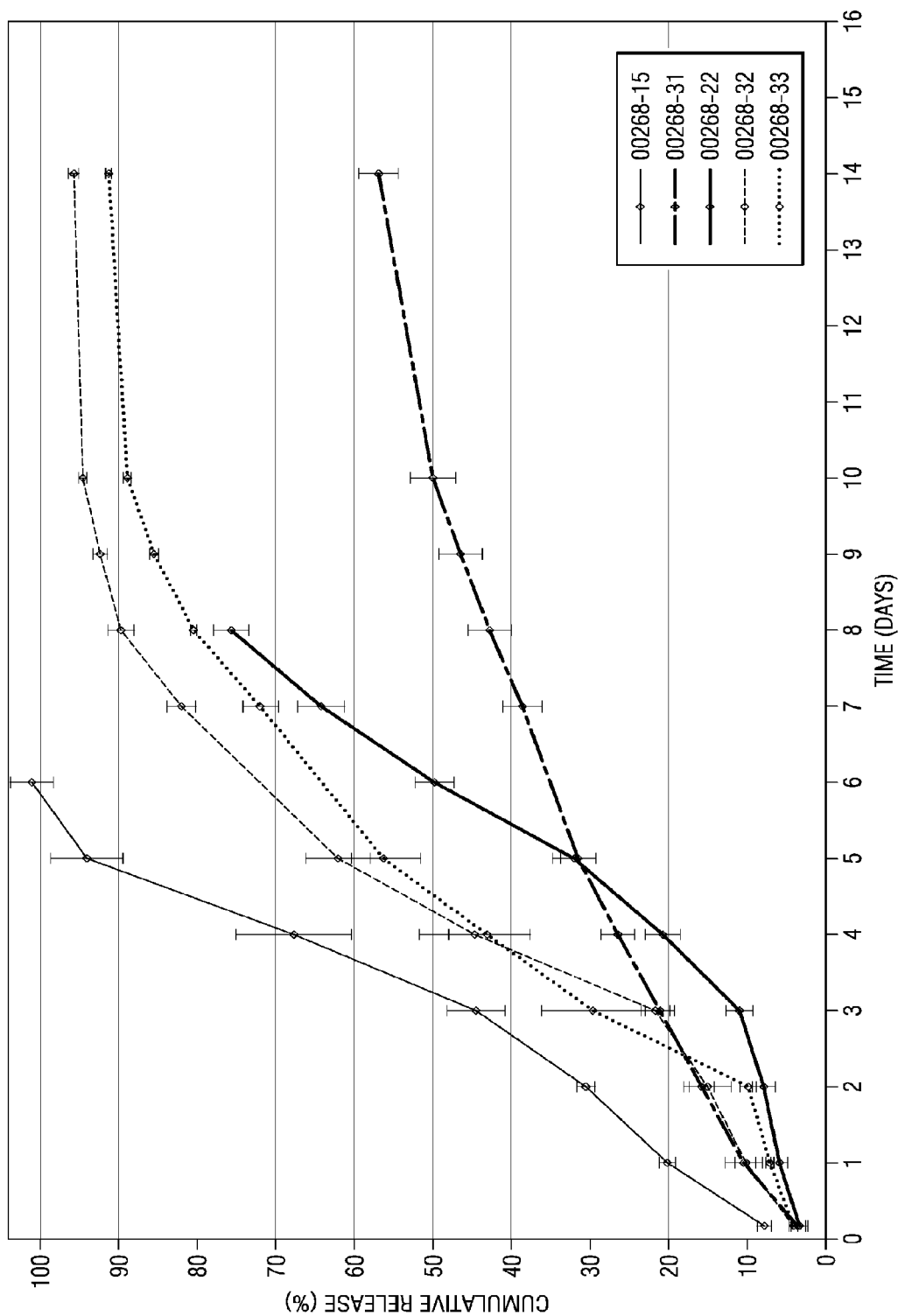
FIG. 9 is a graphic representation of the average percentage cumulative release of clonidine during days 1-14 for certain clonidine HCl strip or ribbon depots illustrated in FIG. 5.
Figure 10:
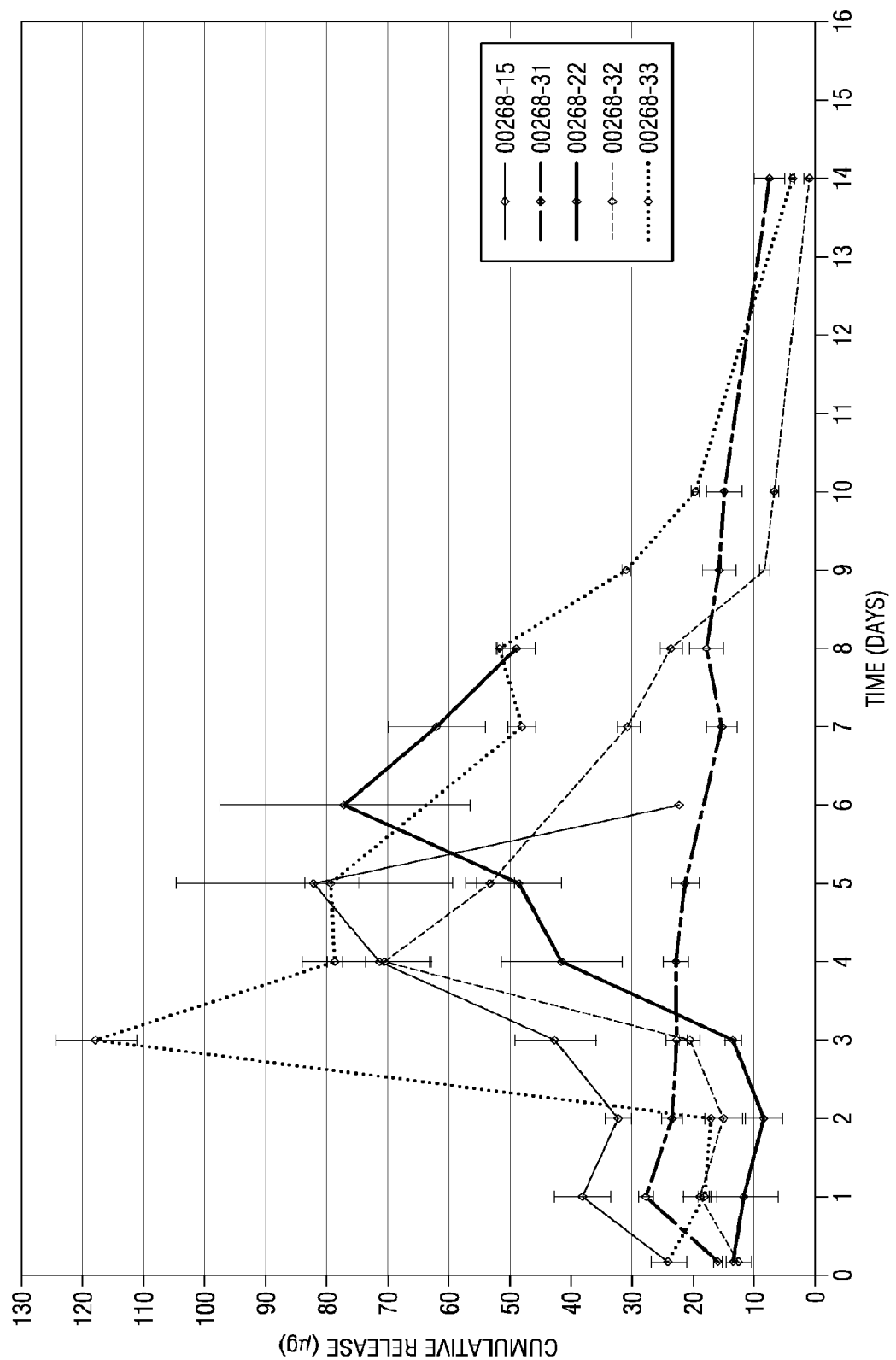
FIG. 10 is a graphic representation of the average daily release of clonidine during days 1-14 for the certain clonidine HCl strip or ribbon depots illustrated in FIG. 9.
Figure 11:
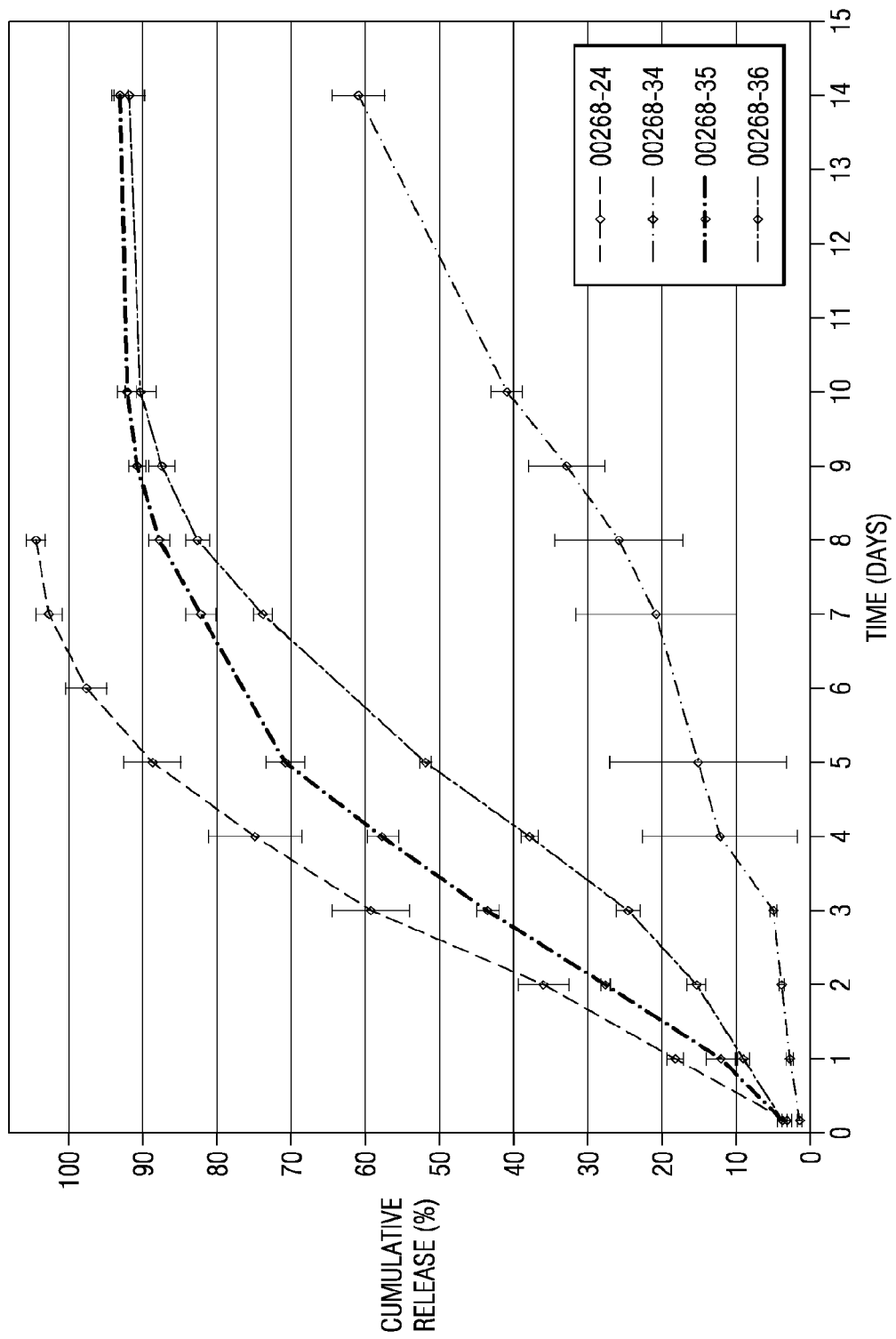
FIG. 11 is a graphic representation of the average percentage cumulative release of clonidine during days 1-14 for certain clonidine HCl strip or ribbon depots illustrated in FIG. 5.
Figure 12:
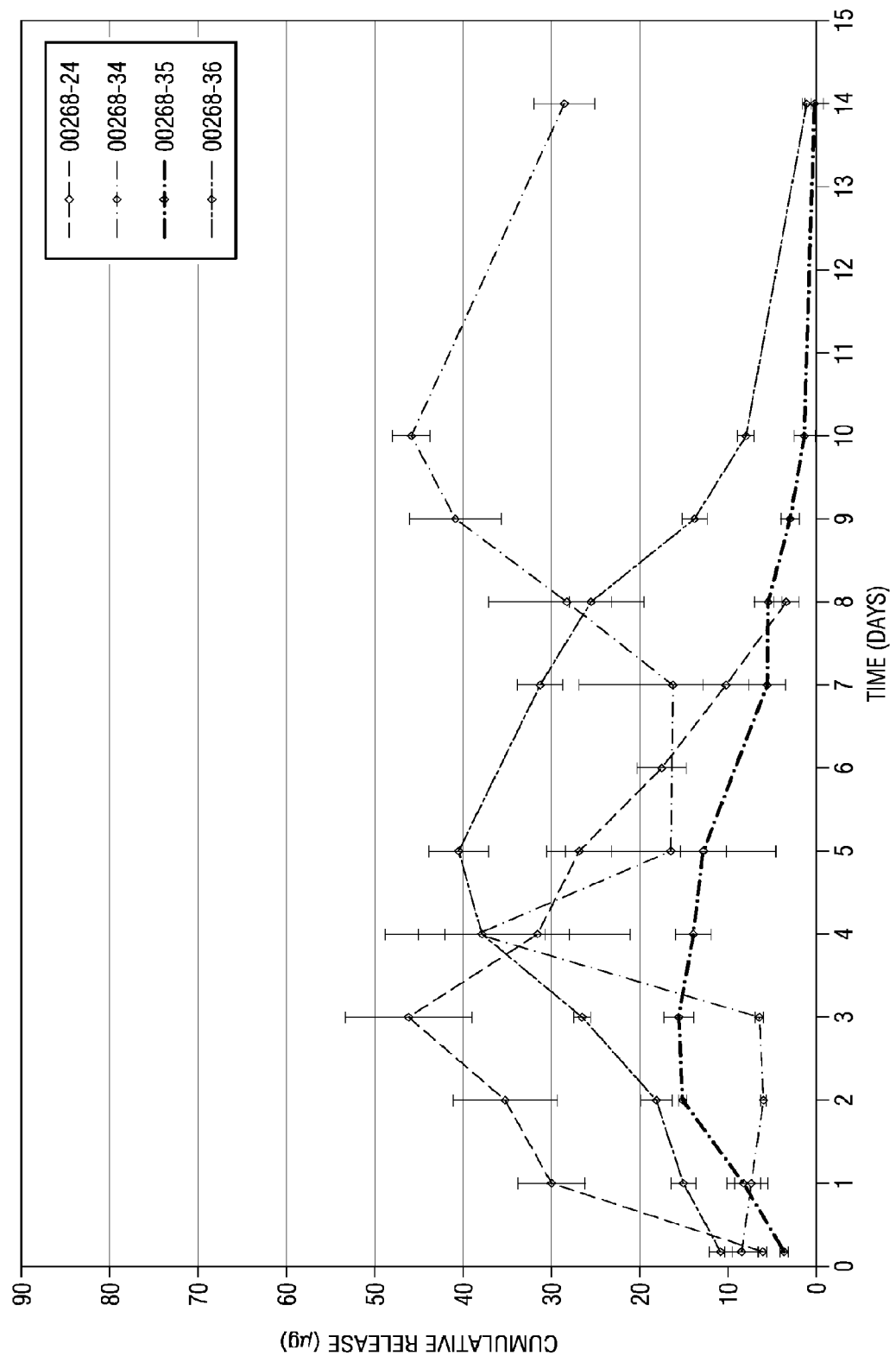
FIG. 12 is a graphic representation of the average daily release of clonidine during days 1-14 for the certain clonidine HCl strip or ribbon depots illustrated in FIG. 11.

In Vitro Drug Elution Testing: Each strip from the batch numbers from Table 2 was tested in triplicate and placed in 4 mL scintillation vials for drug elution testing. Each strip or ribbon was incubated in 2 mL of phosphate buffered saline pH 7.4 (Hyclone) at 37° C. under mild agitation. At pre-selected time points, the buffer was removed for analysis and replaced with fresh buffer medium. The drug content was quantified by HPLC. FIGS. 5 and 6 show the average release rate of clonidine in percentages and micrograms, respectively, for strips of the batch numbers from Table 2 during days 1-8. FIGS. 7 and 8 show the average release rate of clonidine in percentages and micrograms, respectively, for strips of batch numbers 00268-15, 00268-24, 00268-31 and 00268-35 from Table 2 during days 1-8. FIGS. 9 and 10 show the average release rate of clonidine in percentages and micrograms, respectively, for strips of batch numbers 00268-15, 00268-22, 00268-31, 00268-32 and 00268-33 from Table 2 during days 1-14. FIGS. 11 and 12 show the average release rate of clonidine in percentages and micrograms, respectively, for strips of batch numbers 00268-24, 00268-34, 00268-35 and 00268-36 from Table 2 during days 1-14.

The inventors were able to achieve a wide range of release profiles including some formulations with burst release initially and some formulations with linear constant release. These formulations were successful in achieving drug release for at least 14 days.

Example 3

Several clonidine HCl depots were prepared in which the drug load was varied. Representative formulations for the strip or ribbon depots are described below in Table 3. A number of tests were performed on the strip or ribbon depots including in vitro release tests in which the number of micrograms released was measured as well as the cumulative percentage release of clonidine. The results of these tests appear in FIG. 13.

Materials: Poly(D,L-lactide-co-glycolide) having a 50:50 lactide to glycolide molar ratio, a molecular weight of 8 kDa, an inherent viscosity of 0.12 dL/g and acid end capped polymer chain ends (5050 DLG 1A) was purchased from Lakeshore Biomaterials (Birmingham, Ala.). Clonidine HCl was purchased from Spectrum Chemicals (Gardena, Calif.). Methoxy polyethylene glycol (mPEG) having an average molecular weight of 550 was purchased from Sigma-Aldrich. Methanol and acetone were also purchased from Sigma-Aldrich.

Method of Preparation of Spray-Dried Clonidine HCl: Clonidine HCl was dissolved in methanol to yield a 12% (w/w) solution. The solution was spray-dried in a Buchi B-290 Mini Spray Dryer (Buchi Laboratorium AG, Switzerland) using a 120 kHz Sono-Tek ultrasonic nozzle (Sono-Tek Corp., Milton, N.Y). The processing parameters were set as follows: inlet temp. (70° C.), aspirator (80%), nitrogen inlet (50 mm), spray flow rate (80 mL/hr) and ultrasonic generator (0.8 watts). The spray-dried powder was collected and dried for additional 24 hours at 70° C. and 15 mmHg vacuum.

Preparation of Melt Extruded Rods: Several formulations were prepared for melt extrusion. All of the formulations contained 5050 DLG 1A ground into powder using a Retsch (Retsch GmbH, Germany) rotor mill with an 80 micrometer sieve filter. All of the formulations contained 10% (w/w) mPEG. The rest of each of the formulations contained 5050 DLG 1A polymer and clonidine HCl with the weight percentages shown in Table 3 below. The formulations were dry mixed with a spatula prior to being feed into a Haake Mini-Lab twin screw extruder (Thermo Fischer Scientific, Waltham, Mass.). The extruder settings were as follows: 70° C. and 30 RPM for all of the formulations. All of the formulations were extruded out of a 1.5 mm diameter die.

Strip Preparation: Extruded formulations were pressed into sheets of a desired thickness using a Carver Laboratory Heat Press (Carver, Inc., Wabash, Ind.) set at 50° C. The sheets were cut by razor blades to form strip or ribbon implants of the desired dimensions for a rat paw. The dimensions of strips or ribbons made from the formulations are provided in Table 3 below.

TABLE 3

| Formulation ID | Polymer | Drug Load (%) | Excipient | Strip Size (mm) (L x W x H) |
|---|---|---|---|---|
| 13335-76-4a | 5050 DLG 1A | 5 | 10% mPEG | 9 x 1.5 x 0.5 |
| 13335-76-4d | 5050 DLG 1A | 5 | 10% mPEG | 9 x 3 x 0.25 |
| 13335-76-5a | 5050 DLG 1A | 2.5 | 10% mPEG | 9 x 3 x 0.5 |
| 13335-76-5d | 5050 DLG 1A | 2.5 | 10% mPEG | 9 x 3 x 0.25 |
| 13335-76-6 | 5050 DLG 1A | 10 | 10% mPEG | 9 x 3 x 0.25 |

Figure 13:
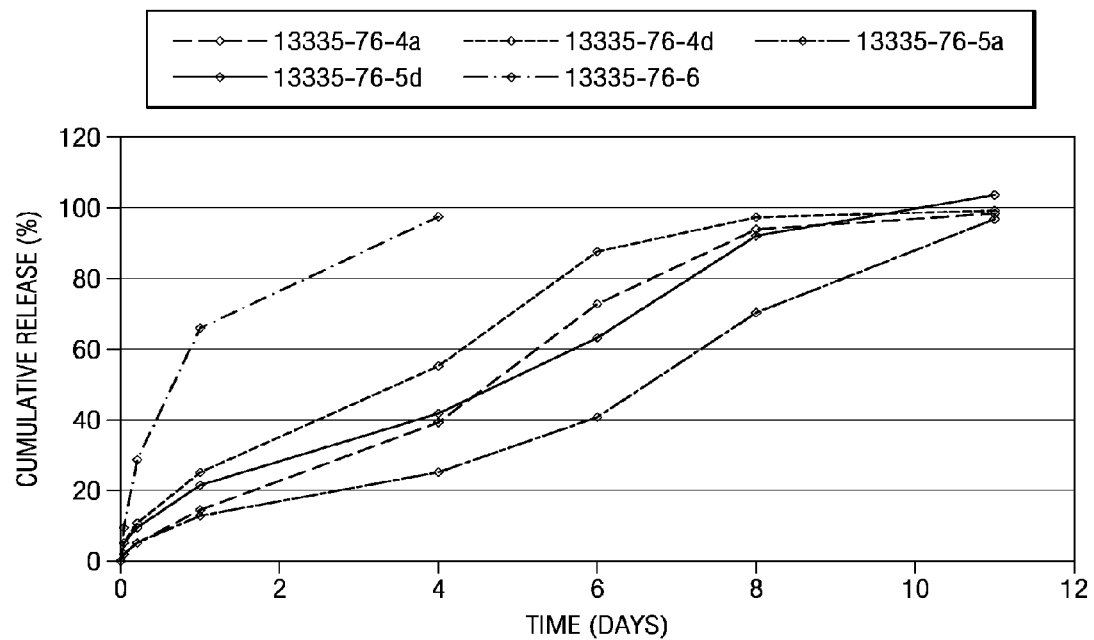
FIG. 13 is a graphic representation of the average cumulative in vitro release profile for clonidine strip depots from a study described in Example 3.

In Vitro Drug Elution Testing: Clonidine strip or ribbon depots made from the formulations from Table 3 were tested in triplicate and placed in 20 mL scintillation vials for drug elution testing. The clonidine strip or ribbon depots were incubated in 5 mL of phosphate buffered saline pH 7.4 (Hyclone) at 37° C. under mild agitation. At pre-selected time points, the buffer was removed for analysis and replaced with fresh buffer medium. The drug content was quantified at 226 nm for clonidine by a Molecular Devices SpectraMax M2 (Sunnyvale, Calif.) plate reader. The drug load for strips from the formulations is shown in Table 3. FIG. 13 shows the average percentage release rate of clonidine for strips from formulation ID Nos. 13335-76-4-a, 13335-76-4-d, 13335-76-5a, 13335-76-5d and 13335-76-6 from Table 3 during days 1-12. Clonidine formulations having an in vitro release profile for the clonidine were successfully formulated for at least 11 days. (FIG. 13).

Example 4

Figure 14:
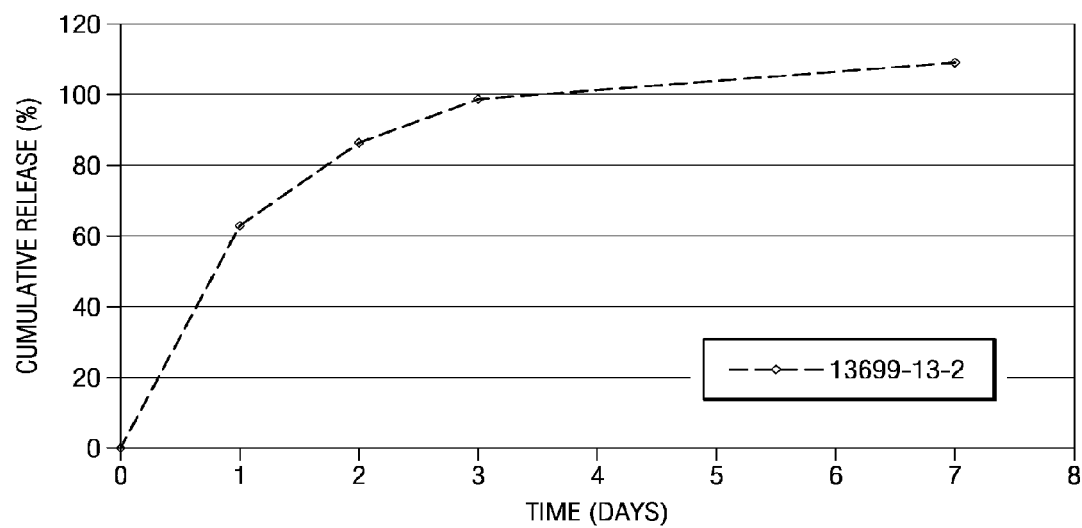
FIG. 14 shows the average cumulative in vitro release profile for clonidine strip implants from a study described in Example 4.

A clonidine HCl gel formulation was prepared. The average in vitro cumulative percentage release of clonidine was measured and is shown in FIG. 14.

Preparation of PLA Gel: Depolymerization of Polylactic Acid with Dodecanol

Polylactic acid (intrinsic viscosity of 5.71 and weight of 15.0 grams), 4-dimethylaminopyridine (Weight of 9.16 grams), and dodecanol (weight of 5.59 grams) were added into a 100 mL round bottom flask, charged, capped with a rubber septum and placed in an oil bath at 140° C. The materials were heated at that temperature for 30 minutes after everything was melted and was stirred freely with a magnetic stir bar. After cooling, 15 mL of tetrahydrofuran was added into the flask to dissolve the materials and precipitated by adding heptane. After decanting off the solvents, the material was dissolved in chloroform (30 mL) and washed with hydrochloride (1 molar, 20 mL, three times) and brined once. The solution was dried over anhydrous sodium sulfate. Yellow oil was obtained after solvent removal by rota-evaporation. (Mn about 800 g/mol by end group analysis by H-NMR)

Method of Preparation of Clonidine HCl Gel Formulation: The formulation was prepared to contain 99% (w/w) PLA gel and 1% (w/w) spray-dried clonidine HCl. The two components were added to a 2 cc transfer cup and mixed in a Flacktek, Inc. Speedmixer DAC 150 FVZ for 2 minutes. The mixed formulation was then back loaded into a 1 mL BD syringe with a 18G 1.5 inch blunt tip needle.

In Vitro Drug Elution Testing: 100 uL of the gel formulation was injected in a 20 mL scintillation vial for drug elution testing. The formulation was tested in triplicate and incubated in 10 mL of phosphate buffer with 0.5% (w/w) sodium dodecyl sulfate pH 7.4 at 37° C. under mild agitation. At pre-selected time points, the buffer was removed for analysis and replaced with fresh buffer medium. The drug content was quantified at 226 nm for clonidine by a Molecular Devices SpectraMax M2 (Sunnyvale, Calif.) plate reader. The resulting formulation (Formulation ID 13699-13-2) included 1% clonidine HCL. FIG. 14 shows the average in vitro cumulative percentage release of clonidine per day for the 3 samples of the formulation that were tested.

Example 5

A clonidine HCl formulation was prepared and a number of tests were performed on strips or ribbons made from the formulation including in vitro release tests in which the number of micrograms released was measured as well as the cumulative percentage release of clonidine. The results of these tests appear in FIGS. 15-18.

Materials: Poly(D,L-lactide-co-glycolide) having a 50:50 lactide to glycolide molar ratio, a molecular weight of 8 kDa, an inherent viscosity of 0.12 dL/g and acid end capped polymer chain ends (5050 DLG 1A) was purchased from Lakeshore Biomaterials (Birmingham, Ala.). Poly(D,L-lactide-co-glycolide) having a 50:50 lactide to glycolide molar ratio, a molecular weight of 58 kDa, an inherent viscosity of 0.43 dL/g and acid end capped polymer chain ends (5050 DLG 4A) was purchased from Lakeshore Biomaterials (Birmingham, Ala.). Clonidine HCl was purchased from Spectrum Chemicals (Gardena, Calif.). Methoxy polyethylene glycol (mPEG) having an average molecular weight of 550 was purchased from Sigma-Aldrich. Methanol was also purchased from Sigma-Aldrich.

Method of Preparation of Spray-Dried Clonidine HCl: Clonidine HCl was dissolved in methanol to yield a 12% (w/w) solution. The solution was spray-dried in a Buchi B-290 Mini Spray Dryer (Buchi Laboratorium AG, Switzerland) using a 120 kHz Sono-Tek ultrasonic nozzle (Sono-Tek Corp., Milton, N.Y). The processing parameters were set as follows: inlet temp. (70° C.), aspirator (80%), nitrogen inlet (50 mm), spray flow rate (80 mL/hr) and ultrasonic generator (0.8 watts). The spray-dried powder was collected and dried for an additional 24 hours at 70° C. and 15 mmHg vacuum.

Preparation of Melt Extruded Rods: The formulation containing 25 wt. % 5050 DLG 1A and 64.5 wt. % 5050DLG 4A was ground into powder using a Retsch (Retsch GmbH, Germany) rotor mill with an 80 micrometer sieve filter. The polymer powder was dry mixed with 10 wt. % mPEG with a spatula prior to being fed into a Laboratory Mixer Molder (Dynisco, Franklin, Mass.) set at 70° C. and max RPM. The polymer mixture was melt mixed for 5 minutes. Next, 0.5 wt. % spray-dried clonidine HCl was added to the polymer melt and mixed for 3 minutes in the mixer molder at 70° C. and max RPM.

Strip Preparation: The mixed formulation was pressed into sheets of a 0.5 mm thickness using a Carver Laboratory Heat Press (Carver, Inc., Wabash, Ind.) set at 50° C. The sheets were cut by razor blades to form strips/ribbons of a desired dimension. The strip depots comprising 25 wt. % 5050 DLG 1A, 64.5 wt. % 5050DLG 4A, 10 wt. % mPEG and 0.5% spray-dried clonidine HCl were then tested for their in vitro release.

In Vitro Drug Elution Testing: Three clonidine strip depots prepared according to the procedure described in this example having the dimensions 20 mm×5 mm×0.5 mm were placed in 20 mL scintillation vials for drug elution testing. The clonidine strips were incubated in 5 mL of phosphate buffered saline pH 7.4 (Hyclone) at 37° C. under mild agitation. At pre-selected time points, the buffer was removed for analysis and replaced with fresh buffer medium. The drug content was quantified at 226 nm for clonidine by a Molecular Devices SpectraMax M2 (Sunnyvale, Calif.) plate reader.

Figure 15:
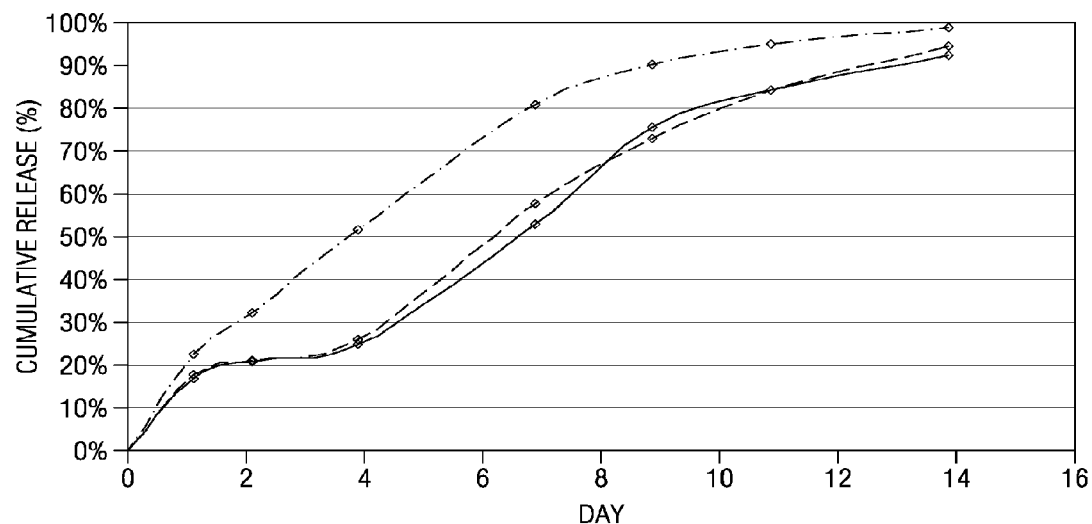
FIG. 15 is a graphic representation of the percentage cumulative release of clonidine for three clonidine strip depots from a study described in Example 5.
Figure 16:
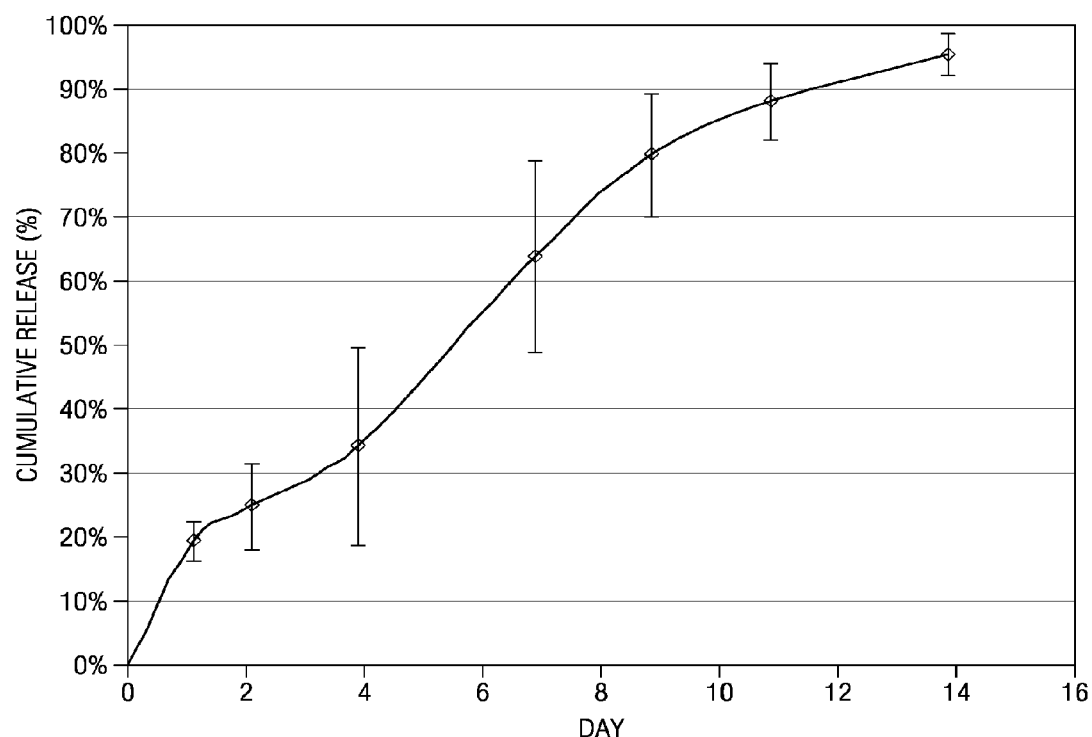
FIG. 16 is a graphic representation of the average percentage cumulative release of clonidine for the clonidine strip depots shown in FIG. 15.

FIGS. 15 and 16 are in vitro graphic representations of the percentage cumulative release of three sterilized clonidine strip depots. As is readily apparent in these figures, each strip released between 90% and 100% of the clonidine over 14 days with an average of 5%-10% of drug released every day. The average cumulative drug release of the three strips is shown in FIG. 16, where 95% of the drug released in 14 days.

Figure 17:
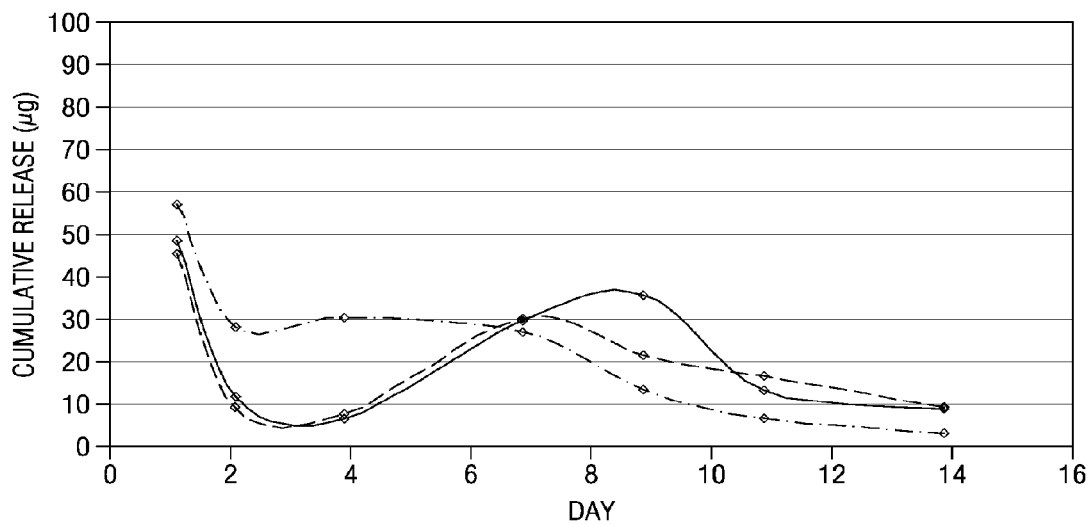
FIG. 17 is a graphic representation of the cumulative in vitro release of clonidine in ug for the three clonidine strip depots described in Example 5.
Figure 18:
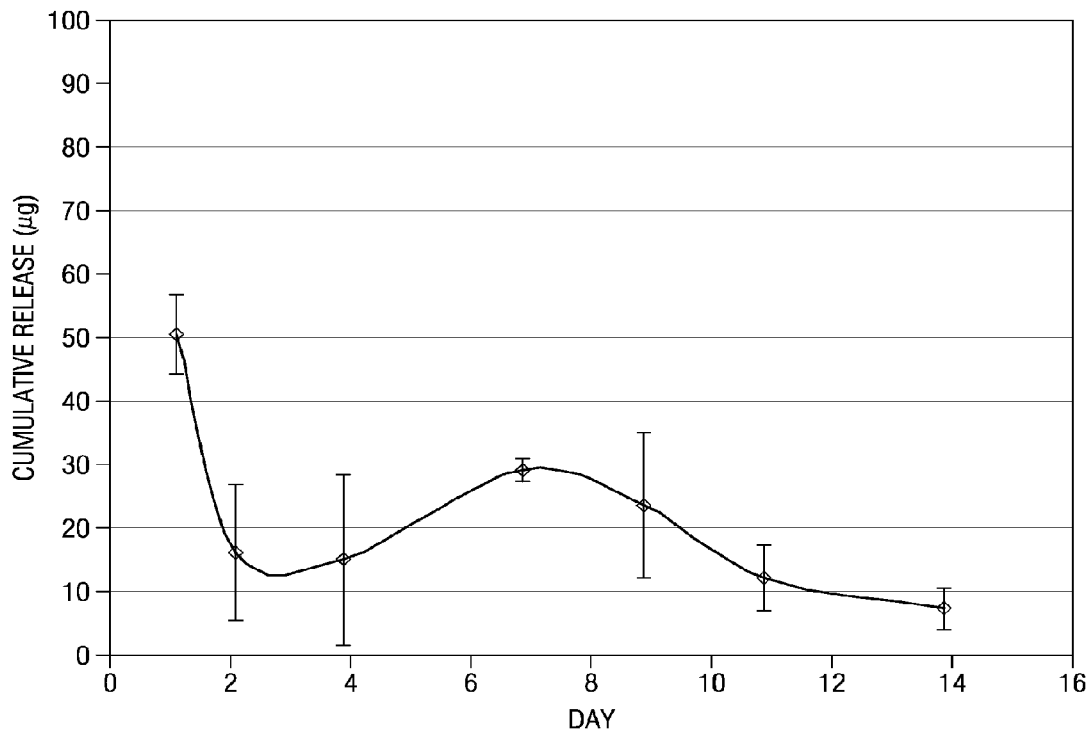
FIG. 18 is a graphic representation of the average cumulative in vitro release of clonidine in ug for the clonidine strip depots shown in FIG. 17.

FIGS. 17 and 18 are in vitro graphic representations of the daily release profile of the three sterilized clonidine strip depots and their cumulative average daily release in micrograms per day. As is readily apparent in these figures, each drug depot had an initial burst effect with a release of clonidine HCl at a dose of about 45 to 60 mcg within about 1 day. After the first day, each drug depot released about 5-35 mcg per day until the drug depot was exhausted at day 14.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of preventing or treating bleeding at a surgical site in a patient, the method comprising implanting one or more biodegradable polymer drug depots comprising a therapeutically effective amount of a clonidine or a pharmaceutically acceptable salt thereof locally to the surgical site to prevent or treat bleeding at the surgical site, wherein the one or more biodegradable polymer drug depots releases an effective amount of the clonidine over a period of at least 3 days following a surgical procedure to treat or prevent bleeding at the surgical site.

2. A method according to claim 1, wherein the one or more biodegradable polymer drug depots releases 0.1 µg to 100 µg of the clonidine over 24 to 48 hours for a period of at least 3 days to prevent or treat the bleeding at the surgical site.

3. A method according to claim 1, wherein the polymer comprises about 70% to about 90% of the total weight % of the one or more biodegradable polymer drug depots.

4. A method according to claim 1, wherein the one or more biodegradable polymer drug depots releases (i) a bolus dose of the clonidine at the surgical site over a period up to 48 hours and (ii) an effective amount of the clonidine over a subsequent period of at least 3 days.

5. A method according to claim 1, wherein the one or more biodegradable polymer drug depots is disposed on or within a medical device and the one or more biodegradable polymer drug depots releases the clonidine or the pharmaceutically acceptable salt thereof over a period of 3 to 7 days.

6. A method according to claim 1, wherein the biodegradable polymer comprises one or more of poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone or a combination thereof.

7. A method according to claim 1, wherein the biodegradable polymer comprises about 60% to 99% of the total weight % of the one or more biodegradable polymer drug depots.

8. A method according to claim 1, wherein the one or more biodegradable polymer drug depots releases about 20% to about 99% of the clonidine relative to a total amount of the clonidine loaded in the one or more biodegradable polymer drug depots over a period of 3 to 7 days after the one or more biodegradable polymer drug depots is administered to the surgical site.

9. A method according to claim 1, wherein the biodegradable polymer is capable of degrading in 30 days or less after the one or more biodegradable polymer drug depots is implanted at the surgical site.

10. A method according to claim 1, wherein the clonidine is released in an amount between 0.05 µg and 3 mg per day for a period of 3 to 10 days to prevent, reduce or treat bleeding at the surgical site.

11. A method according to claim 1, wherein the clonidine is present in an amount of about 0.1 to about 10 wt. % of the one or more biodegradable polymer drug depots and the polymer is present in an amount of about 75 to about 94 wt. % of the one or more biodegradable polymer drug depots, and the one or more biodegradable polymer drug depots further comprises from about 5 to about 15 wt. % of an excipient.

12. A method according to claim 1, wherein the clonidine is present in an amount of about 0.1 to about 10 wt. % of the one or more biodegradable polymer drug depots and the polymer comprises PLGA in an amount of about 75 to about 94 wt. % of the one or more biodegradable polymer drug depots, and the one or more biodegradable polymer drug depots further comprises from about 5 to about 15 wt. % mPEG.

13. A method according to claim 1, wherein the one or more biodegradable polymer drug depots can reduce or treat bleeding at the surgical site within 1 hour after implantation.

14. A method of preventing or treating bleeding at a surgical site in a patient, the method comprising administering one or more biodegradable drug depots comprising a therapeutically effective amount of clonidine or a pharmaceutically acceptable salt thereof in a polymer; wherein the one or more biodegradable drug depots is implantable locally at the surgical site to reduce, prevent or treat bleeding, and the one or more biodegradable drug depots is capable of releasing (i) about 5% to about 45% of the clonidine relative to a total amount of the clonidine loaded in the one or more biodegradable drug depots over a first period of up to 48 hours following a surgical procedure to treat or prevent bleeding at the surgical site and (ii) about 55% to about 99% of the clonidine relative to a total amount of the clonidine loaded in the one or more biodegradable drug depots over a subsequent period of at least 3 days following the surgical procedure to treat or prevent bleeding at the surgical site.

15. A method according to claim 14, wherein the polymer comprises one or more of poly(lactide-co-glycolide), polylactide, polyglycolide, polyorthoester, D-lactide, D,L-lactide, poly(D,L-lactide), L-lactide, poly(D,L-lactide-co-caprolactone), poly(D,L-lactide-co-glycolide-co-caprolactone), polycaprolactone or a combination thereof.

16. A method according to claim 14, wherein the polymer comprises about 60% to about 90% of the total wt. % of the one or more biodegradable drug depots.

17. A method according to claim 14, wherein the polymer is capable of degrading in 30 days or less after the one or more biodegradable drug depots is implanted at the surgical site.

18. A method according to claim 14, wherein the clonidine is released in an amount between 0.05 µg and 3 mg per day during the subsequent period for at least 3 to 10 days to prevent, reduce or treat bleeding at the surgical site.

19. A method according to claim 14, wherein the one or more biodegradable drug depots can prevent, reduce or treat bleeding at the surgical site within 1 hour after implantation.

* * * * *